(12) United States Patent
Gyrn et al.

(10) Patent No.: US 10,898,643 B2
(45) Date of Patent: Jan. 26, 2021

(54) SEALING BETWEEN A CANNULA PART AND A FLUID PATH

(75) Inventors: Steffen Gyrn, Ringsted (DK); Elo Lau Hørdum, Hørsholm (DK)

(73) Assignee: UNOMEDICAL A/S, Birkeroed (DK)

( * ) Notice: Subject to any disclaimer, the term of this patent is extended or adjusted under 35 U.S.C. 154(b) by 576 days.

(21) Appl. No.: 12/865,566

(22) PCT Filed: Feb. 12, 2009

(86) PCT No.: PCT/EP2009/051634
§ 371 (c)(1),
(2), (4) Date: Oct. 27, 2010

(87) PCT Pub. No.: WO2009/101130
PCT Pub. Date: Aug. 20, 2009

(65) Prior Publication Data
US 2011/0034883 A1    Feb. 10, 2011

Related U.S. Application Data

(60) Provisional application No. 61/028,259, filed on Feb. 13, 2008.

(30) Foreign Application Priority Data

Feb. 13, 2008  (DK) ................. 2008 00202

(51) Int. Cl.
| | | |
|---|---|---|
| *A61M 29/00* | (2006.01) | |
| *A61M 5/178* | (2006.01) | |
| *A61M 5/315* | (2006.01) | |
| *A61M 5/158* | (2006.01) | |
| *A61M 5/142* | (2006.01) | |
| *A61M 39/26* | (2006.01) | |
| *A61M 5/14* | (2006.01) | |

(52) U.S. Cl.
CPC ........ *A61M 5/158* (2013.01); *A61M 5/14248* (2013.01); *A61M 5/1413* (2013.01);
(Continued)

(58) Field of Classification Search
CPC ................ A61M 5/14; A61M 5/14244; A61M 5/14248; A61M 5/14276; A61M 5/145;
(Continued)

(56) References Cited

U.S. PATENT DOCUMENTS

| | | |
|---|---|---|
| 1,592,462 A | 7/1926 | MacGregor |
| 2,047,010 A | 7/1936 | Dickinson |

(Continued)

FOREIGN PATENT DOCUMENTS

| | | |
|---|---|---|
| DE | 4 342 329 A1 | 6/1994 |
| DE | 196 31 921 A1 | 3/1997 |

(Continued)

OTHER PUBLICATIONS

International Search Report dated May 13, 2009 for International Application No. PCT/EP2009/051634.
(Continued)

*Primary Examiner* — Rebecca E Eisenberg
(74) *Attorney, Agent, or Firm* — Taft Stettinius & Hollister LLP; Ryan O. White; Derek B. Lavender

(57) ABSTRACT

The application relates to an infusion part comprising a cannula part (7) and a fluid path, whereby a sealing (18) is positioned between the cannula part and an inlet/outlet opening (12) of the fluid path when the cannula part is in position for use in order to keep the fluid path to a cannula tight. The sealing (18) is surrounding the inlet/outlet opening (12) and/ or the distance $d_1$ between a centre line c of the cannula part and a point on an outer surface of the cannula part positioned at or above an upper edge of the sealing (18) is larger than the distance $d_2$ between the centre line c of the cannula part and a point on the outer surface of the cannula part positioned at or below a lower edge of the sealing.

19 Claims, 15 Drawing Sheets

(52) U.S. Cl.
CPC ............ *A61M 2005/14252* (2013.01); *A61M 2005/1581* (2013.01); *A61M 2005/1585* (2013.01); *A61M 2005/1587* (2013.01); *A61M 2039/267* (2013.01)

(58) Field of Classification Search
CPC .................. A61M 5/158; A61M 5/162; A61M 2005/14252; A61M 2005/1581; A61M 2005/1585; A61M 2005/1586; A61M 2005/1587; A61M 2025/0004; A61M 25/0097; A61M 2025/0175; A61M 25/0606; A61M 5/1413
USPC ........... 604/244, 523, 93.01, 164.01, 164.04, 604/167.01, 167.02, 180, 513
See application file for complete search history.

(56) References Cited

U.S. PATENT DOCUMENTS

| | | | |
|---|---|---|---|
| 2,295,849 A | 9/1942 | Kayden | |
| 2,690,529 A | 9/1954 | Lindblad | |
| 2,972,779 A | 2/1961 | Cowley | |
| 3,059,802 A | 10/1962 | Mitchell | |
| 3,074,541 A | 10/1963 | Roehr | |
| 3,149,186 A | 9/1964 | Coanda | |
| 3,221,739 A | 12/1965 | Rosenthal | |
| 3,221,740 A | 12/1965 | Rosenthal | |
| 3,306,291 A | 2/1967 | Burke | |
| 3,485,352 A | 12/1969 | Pilger | |
| 3,509,879 A | 5/1970 | Bathish et al. | |
| 3,519,158 A | 7/1970 | Anderson | |
| 3,547,119 A | 12/1970 | Hall et al. | |
| 3,575,337 A | 4/1971 | Bernhardt | |
| 3,610,240 A | 10/1971 | Harautuneian | |
| 3,615,039 A | 10/1971 | Ward | |
| 3,670,727 A | 6/1972 | Reiterman | |
| 3,783,895 A | 1/1974 | Weichselbaum | |
| 3,788,374 A | 1/1974 | Saijo | |
| 3,810,469 A | 5/1974 | Hurschman | |
| 3,835,862 A | 9/1974 | Villari | |
| 3,840,011 A | 10/1974 | Wright | |
| 3,893,448 A | 7/1975 | Brantigan | |
| 3,937,219 A | 2/1976 | Karakashian | |
| 3,986,507 A | 10/1976 | Watt | |
| 3,986,508 A | 10/1976 | Barrington | |
| 3,995,518 A | 12/1976 | Spiroff | |
| 4,022,205 A | 5/1977 | Tenczar | |
| 4,188,950 A | 2/1980 | Wardlaw | |
| 4,201,406 A | 5/1980 | Dennehey et al. | |
| 4,227,528 A | 10/1980 | Wardlaw | |
| 4,259,276 A | 3/1981 | Rawlings | |
| 4,267,836 A | 5/1981 | Whitney et al. | |
| 4,296,786 A | 10/1981 | Brignola | |
| 4,315,505 A | 2/1982 | Crandall et al. | |
| 4,333,455 A | 6/1982 | Bodicky | |
| 4,334,551 A | 6/1982 | Pfister | |
| D267,199 S | 12/1982 | Koenig | |
| 4,378,015 A | 3/1983 | Wardlaw | |
| 4,402,407 A | 9/1983 | Maly | |
| 4,415,393 A | 11/1983 | Grimes | |
| 4,417,886 A | 11/1983 | Frankhouser et al. | |
| 4,464,178 A | 8/1984 | Dalton | |
| 4,473,369 A | 9/1984 | Lueders et al. | |
| 4,484,910 A | 11/1984 | Sarnoff et al. | |
| 4,500,312 A | 2/1985 | McFarlane | |
| 4,508,367 A | 4/1985 | Oreopoulos et al. | |
| 4,525,157 A | 6/1985 | Vaillancourt | |
| 4,530,695 A | 7/1985 | Phillips et al. | |
| 4,531,937 A | 7/1985 | Yates | |
| 4,543,088 A | 9/1985 | Bootman et al. | |
| 4,563,177 A | 1/1986 | Kamen | |
| 4,610,469 A | 9/1986 | Wolff-Mooij | |
| 4,617,019 A | 10/1986 | Fecht | |
| 4,713,059 A | 12/1987 | Bickelhaupt et al. | |
| 4,734,092 A | 3/1988 | Millerd | |
| 4,755,173 A * | 7/1988 | Konopka et al. | ........ 604/167.02 |
| 4,817,603 A | 4/1989 | Turner et al. | |
| RE32,922 E | 5/1989 | Levin et al. | |
| 4,838,871 A | 6/1989 | Luther | |
| 4,840,613 A | 6/1989 | Balbierz | |
| 4,850,974 A | 7/1989 | Bickelhaupt et al. | |
| 4,850,996 A | 7/1989 | Cree | |
| 4,863,016 A | 9/1989 | Fong et al. | |
| 4,878,897 A | 11/1989 | Katzin | |
| 4,890,608 A | 1/1990 | Steer | |
| 4,894,054 A | 1/1990 | Miskinyar | |
| 4,895,570 A | 1/1990 | Larkin | |
| 4,917,669 A | 4/1990 | Bonaldo | |
| 4,935,010 A | 6/1990 | Cox et al. | |
| 4,950,163 A | 8/1990 | Zimble | |
| 4,950,252 A | 8/1990 | Luther et al. | |
| 4,956,989 A | 9/1990 | Nakajima | |
| 4,970,954 A | 11/1990 | Weir et al. | |
| 4,978,338 A | 12/1990 | Melsky et al. | |
| 4,982,842 A | 1/1991 | Hollister | |
| 4,986,817 A | 1/1991 | Code | |
| 4,994,042 A | 2/1991 | Vadher | |
| 4,994,045 A | 2/1991 | Ranford | |
| 5,011,475 A | 4/1991 | Olson | |
| 5,020,665 A | 6/1991 | Bruno | |
| 5,024,662 A | 6/1991 | Menes et al. | |
| 5,067,496 A | 11/1991 | Eisele | |
| 5,092,853 A | 3/1992 | Couvertier, II | |
| 5,098,389 A | 3/1992 | Cappucci | |
| 5,112,313 A | 5/1992 | Sallee | |
| 5,116,319 A | 5/1992 | Van den Haak | |
| 5,116,325 A | 5/1992 | Paterson | |
| 5,121,751 A | 6/1992 | Panalletta | |
| 5,129,884 A | 7/1992 | Dysarz | |
| 5,135,502 A | 8/1992 | Koenig, Jr. et al. | |
| 5,137,516 A | 8/1992 | Rand et al. | |
| 5,137,524 A | 8/1992 | Lynn et al. | |
| 5,141,496 A | 8/1992 | Dalto et al. | |
| 5,147,375 A | 9/1992 | Sullivan et al. | |
| 5,160,315 A | 11/1992 | Heinecke et al. | |
| 5,163,915 A | 11/1992 | Holleron | |
| 5,172,808 A | 12/1992 | Bruno | |
| 5,176,643 A | 1/1993 | Kramer et al. | |
| 5,176,650 A | 1/1993 | Haining | |
| 5,176,662 A * | 1/1993 | Bartholomew et al. | ...... 604/513 |
| 5,186,712 A | 2/1993 | Kelso et al. | |
| 5,188,611 A | 2/1993 | Orgain | |
| RE34,223 E | 4/1993 | Bonaldo | |
| 5,205,820 A | 4/1993 | Kriesel | |
| 5,222,947 A | 6/1993 | D'Amico | |
| 5,232,454 A | 8/1993 | Hollister | |
| 5,248,301 A | 9/1993 | Koenig et al. | |
| 5,256,149 A | 10/1993 | Banik et al. | |
| 5,256,152 A | 10/1993 | Marks | |
| 5,257,980 A | 11/1993 | Van Antwerp et al. | |
| 5,267,963 A | 12/1993 | Bachynsky | |
| 5,269,799 A | 12/1993 | Daniel | |
| 5,271,744 A | 12/1993 | Kramer et al. | |
| 5,279,558 A * | 1/1994 | Kriesel | ........................... 604/85 |
| 5,279,579 A | 1/1994 | D'Amico | |
| 5,279,591 A | 1/1994 | Simon | |
| 5,282,793 A | 2/1994 | Larson | |
| 5,300,030 A | 4/1994 | Crossman et al. | |
| 5,312,359 A | 5/1994 | Wallace | |
| 5,312,369 A | 5/1994 | Arcusin et al. | |
| 5,316,246 A | 5/1994 | Scott et al. | |
| 5,324,302 A | 6/1994 | Crouse | |
| 5,342,319 A | 8/1994 | Watson et al. | |
| 5,342,324 A | 8/1994 | Tucker | |
| 5,344,007 A | 9/1994 | Nakamura et al. | |
| 5,350,392 A | 9/1994 | Purcell et al. | |
| 5,354,280 A | 10/1994 | Haber et al. | |
| 5,354,337 A | 10/1994 | Hoy | |
| 5,366,469 A | 11/1994 | Steg et al. | |
| 5,372,592 A | 12/1994 | Gambale | |
| 5,372,787 A | 12/1994 | Ritter | |
| 5,376,082 A | 12/1994 | Phelps | |
| 5,379,895 A | 1/1995 | Foslien | |
| 5,384,174 A | 1/1995 | Ward et al. | |

(56) References Cited

U.S. PATENT DOCUMENTS

| | | |
|---|---|---|
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,629 A | 5/1996 | Heinecke et al. |
| 5,520,654 A | 5/1996 | Wahlberg |
| 5,522,803 A | 6/1996 | Teissen-Simony |
| 5,527,287 A | 6/1996 | Miskinyar et al. |
| 5,533,974 A | 7/1996 | Gaba |
| 5,540,709 A | 7/1996 | Ramel |
| 5,545,143 A * | 8/1996 | Fischell ............ 604/180 |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,776,103 A * | 7/1998 | Kriesel et al. ............ 604/132 |
| 5,807,316 A | 9/1998 | Teeple |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Petersen et al. |
| D417,733 S | 12/1999 | Howell et al. |
| 6,017,328 A * | 1/2000 | Fischell et al. ............ 604/180 |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stardella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,261,272 B1 | 7/2001 | Gross et al. |
| 6,283,744 B1 | 9/2001 | Edmondson et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse et al. |
| 6,378,218 B2 | 4/2002 | Sigwart et al. |
| 6,379,335 B1 | 4/2002 | Rigon et al. |
| 6,387,076 B1 | 5/2002 | Van Landuyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |

(56) References Cited

U.S. PATENT DOCUMENTS

| | | | |
|---|---|---|---|
| D472,316 S | 3/2003 | Douglas et al. | |
| D472,630 S | 4/2003 | Douglas et al. | |
| 6,572,586 B1 | 6/2003 | Wojcik | |
| 6,579,267 B2 | 6/2003 | Lynch et al. | |
| 6,582,397 B2 | 6/2003 | Alesi et al. | |
| 6,595,962 B1 | 7/2003 | Perthu | |
| 6,607,509 B2 | 8/2003 | Bobroff et al. | |
| 6,607,511 B2 | 8/2003 | Halseth et al. | |
| 6,613,064 B2 | 9/2003 | Rutynowski et al. | |
| 6,620,133 B1 | 9/2003 | Steck | |
| 6,620,136 B1 | 9/2003 | Pressly, Sr. et al. | |
| 6,620,140 B1 | 9/2003 | Metzger | |
| 6,629,949 B1 | 10/2003 | Douglas | |
| 6,645,181 B1 | 11/2003 | Gilad et al. | |
| 6,645,182 B1 | 11/2003 | Szabo | |
| 6,659,982 B2 | 12/2003 | Douglas et al. | |
| 6,685,674 B2 | 2/2004 | Douglas et al. | |
| 6,699,218 B2 | 3/2004 | Flaherty et al. | |
| 6,702,779 B2 | 3/2004 | Connelly et al. | |
| 6,726,649 B2 | 4/2004 | Swenson et al. | |
| 6,736,797 B1 | 5/2004 | Larsen et al. | |
| 6,743,203 B1 | 6/2004 | Pickhard | |
| 6,749,587 B2 | 6/2004 | Flaherty | |
| 6,749,589 B1 | 6/2004 | Douglas et al. | |
| 6,755,805 B1 | 6/2004 | Reid | |
| 6,776,775 B1 | 8/2004 | Mohammad | |
| 6,790,199 B1 | 9/2004 | Gianakos | |
| 6,805,686 B1 | 10/2004 | Fathallah et al. | |
| 6,808,506 B2 | 10/2004 | Lastovich et al. | |
| 6,811,545 B2 | 11/2004 | Vaillancourt | |
| 6,814,720 B2 | 11/2004 | Olsen et al. | |
| 6,824,530 B2 | 11/2004 | Wagner et al. | |
| 6,824,531 B1 | 11/2004 | Zecha, Jr. et al. | |
| 6,830,562 B2 | 12/2004 | Mogensen et al. | |
| 6,837,877 B2 | 1/2005 | Zurcher | |
| 6,837,878 B2 | 1/2005 | Smutney et al. | |
| 6,840,922 B2 | 1/2005 | Nielsen et al. | |
| 6,880,701 B2 | 4/2005 | Bergeron et al. | |
| 6,923,791 B2 * | 8/2005 | Douglas | 604/167.05 |
| 6,926,694 B2 | 8/2005 | Marano-Ford et al. | |
| 6,939,324 B2 * | 9/2005 | Gonnelli et al. | 604/142 |
| 6,939,331 B2 | 9/2005 | Ohshima | |
| 6,949,084 B2 | 9/2005 | Marggi et al. | |
| 6,959,812 B2 | 11/2005 | Reif et al. | |
| 6,960,193 B2 | 11/2005 | Rosenberg | |
| 6,979,316 B1 | 12/2005 | Rubin et al. | |
| 6,991,619 B2 | 1/2006 | Marano-Ford et al. | |
| 6,991,620 B2 | 1/2006 | Marano-Ford et al. | |
| 6,994,213 B2 | 2/2006 | Giard et al. | |
| 6,997,907 B2 | 2/2006 | Safabash et al. | |
| 7,014,625 B2 | 3/2006 | Bengtsson | |
| 7,018,344 B2 | 3/2006 | Bressler et al. | |
| 7,022,108 B2 | 4/2006 | Marano-Ford et al. | |
| 7,047,070 B2 | 5/2006 | Wilkenson et al. | |
| 7,052,483 B2 | 5/2006 | Wojcik | |
| 7,055,713 B2 | 6/2006 | Rea et al. | |
| 7,056,302 B2 | 6/2006 | Douglas | |
| 7,070,580 B2 | 7/2006 | Nielsen | |
| 7,074,208 B2 | 7/2006 | Pajunk et al. | |
| D526,409 S | 8/2006 | Nielsen et al. | |
| 7,083,592 B2 | 8/2006 | Lastovich et al. | |
| 7,083,597 B2 | 8/2006 | Lynch et al. | |
| 7,097,631 B2 | 8/2006 | Trautman et al. | |
| 7,109,878 B2 | 9/2006 | Mann et al. | |
| 7,115,108 B2 | 10/2006 | Wilkenson et al. | |
| 7,115,112 B2 | 10/2006 | Mogensen et al. | |
| 7,137,968 B1 | 11/2006 | Burrell et al. | |
| 7,141,023 B2 | 11/2006 | Diermann et al. | |
| 7,147,623 B2 | 12/2006 | Mathiasen | |
| 7,186,236 B2 | 3/2007 | Gibson et al. | |
| 7,211,068 B2 | 5/2007 | Douglas | |
| 7,214,207 B2 | 5/2007 | Lynch et al. | |
| 7,214,215 B2 | 5/2007 | Heinzerling et al. | |
| 7,250,037 B2 | 7/2007 | Shermer et al. | |
| 7,258,680 B2 | 8/2007 | Mogensen et al. | |
| D554,253 S | 10/2007 | Kornerup | |
| 7,303,543 B1 | 12/2007 | Maule et al. | |
| 7,309,326 B2 | 12/2007 | Fangrow, Jr. | |
| 7,322,473 B2 | 1/2008 | Fux | |
| 7,331,939 B2 | 2/2008 | Fangrow, Jr. | |
| 7,407,491 B2 | 8/2008 | Fangrow, Jr. | |
| 7,407,493 B2 * | 8/2008 | Cane' | 604/181 |
| 7,431,876 B2 | 10/2008 | Mejlhede et al. | |
| 7,441,655 B1 | 10/2008 | Hoftman | |
| 7,569,262 B2 | 8/2009 | Szabo et al. | |
| 7,648,494 B2 | 1/2010 | Kornerup et al. | |
| 7,713,258 B2 | 5/2010 | Adams et al. | |
| 7,766,867 B2 | 8/2010 | Lynch et al. | |
| 7,846,132 B2 * | 12/2010 | Gravesen et al. | 604/164.01 |
| 7,850,652 B2 | 12/2010 | Liniger et al. | |
| 8,012,126 B2 * | 9/2011 | Tipsmark et al. | 604/154 |
| 8,087,333 B2 | 1/2012 | Oishi | |
| 8,123,724 B2 | 2/2012 | Gillespie, III | |
| 8,303,549 B2 * | 11/2012 | Mejlhede et al. | 604/244 |
| 8,323,250 B2 | 12/2012 | Chong et al. | |
| 2001/0004970 A1 | 6/2001 | Hollister et al. | |
| 2001/0016714 A1 | 8/2001 | Bell et al. | |
| 2001/0021827 A1 | 9/2001 | Ferguson et al. | |
| 2001/0039387 A1 | 11/2001 | Rutynowski et al. | |
| 2001/0039401 A1 | 11/2001 | Ferguson et al. | |
| 2001/0041875 A1 | 11/2001 | Higuchi et al. | |
| 2001/0049496 A1 | 12/2001 | Kirchhofer | |
| 2001/0053889 A1 | 12/2001 | Marggi | |
| 2001/0056284 A1 | 12/2001 | Purcell et al. | |
| 2002/0022798 A1 | 2/2002 | Connelly | |
| 2002/0022855 A1 | 2/2002 | Bobroff et al. | |
| 2002/0026152 A1 | 2/2002 | Bierman | |
| 2002/0055711 A1 | 5/2002 | Lavi et al. | |
| 2002/0068904 A1 | 6/2002 | Pluth et al. | |
| 2002/0072720 A1 | 6/2002 | Hague et al. | |
| 2002/0074345 A1 | 6/2002 | Scheider et al. | |
| 2002/0077599 A1 | 6/2002 | Wojcik | |
| 2002/0082543 A1 | 6/2002 | Park et al. | |
| 2002/0107489 A1 | 8/2002 | Lee | |
| 2002/0111581 A1 | 8/2002 | Sasso | |
| 2002/0156424 A1 | 10/2002 | Suzuki et al. | |
| 2002/0156427 A1 | 10/2002 | Suzuki et al. | |
| 2002/0161322 A1 | 10/2002 | Utterberg et al. | |
| 2002/0161332 A1 | 10/2002 | Ramey | |
| 2002/0161386 A1 | 10/2002 | Halseth et al. | |
| 2002/0165493 A1 | 11/2002 | Bierman | |
| 2002/0169419 A1 | 11/2002 | Steg | |
| 2002/0173748 A1 | 11/2002 | McConnell et al. | |
| 2002/0173769 A1 | 11/2002 | Gray et al. | |
| 2002/0183688 A1 | 12/2002 | Lastovich et al. | |
| 2002/0189688 A1 | 12/2002 | Roorda | |
| 2002/0193737 A1 | 12/2002 | Popovsky | |
| 2002/0193744 A1 | 12/2002 | Alesi et al. | |
| 2003/0014018 A1 | 1/2003 | Giambattista et al. | |
| 2003/0060781 A1 | 3/2003 | Mogensen et al. | |
| 2003/0069548 A1 | 4/2003 | Connelly et al. | |
| 2003/0088238 A1 | 5/2003 | Poulsen et al. | |
| 2003/0105430 A1 | 6/2003 | Lavi et al. | |
| 2003/0109829 A1 | 6/2003 | Mogensen et al. | |
| 2003/0125669 A1 | 7/2003 | Safabash et al. | |
| 2003/0125678 A1 | 7/2003 | Swenson et al. | |
| 2003/0130619 A1 | 7/2003 | Safabash et al. | |
| 2003/0139704 A1 | 7/2003 | Lin | |
| 2003/0149405 A1 * | 8/2003 | Enns | 604/273 |
| 2003/0158520 A1 | 8/2003 | Safabash et al. | |
| 2003/0176843 A1 | 9/2003 | Wilkinson | |
| 2003/0176852 A1 | 9/2003 | Lynch et al. | |
| 2003/0181863 A1 | 9/2003 | Davis et al. | |
| 2003/0181868 A1 | 9/2003 | Swenson | |
| 2003/0181873 A1 | 9/2003 | Swenson | |
| 2003/0181874 A1 | 9/2003 | Bressler et al. | |
| 2003/0187394 A1 | 10/2003 | Wilkinson et al. | |
| 2003/0187395 A1 | 10/2003 | Gabel | |
| 2003/0199823 A1 | 10/2003 | Bobroff et al. | |
| 2003/0216686 A1 | 11/2003 | Lynch et al. | |
| 2003/0220610 A1 | 11/2003 | Lastovich et al. | |
| 2003/0225373 A1 | 12/2003 | Bobroff et al. | |
| 2003/0225374 A1 | 12/2003 | Mathiasen | |
| 2003/0229308 A1 | 12/2003 | Tsals et al. | |

(56) References Cited

U.S. PATENT DOCUMENTS

| | | |
|---|---|---|
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0055711 A1 | 3/2004 | Martin et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1* | 8/2004 | Hunn et al. ............... 604/164.01 |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1* | 12/2004 | Bandis ............... A61B 5/14532 600/347 |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1* | 2/2006 | Mogensen ............ A61M 5/158 604/164.01 |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0247553 A1 | 9/2006 | Diermann et al. |
| 2006/0241551 A1 | 10/2006 | Lynch et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049870 A1 | 1/2007 | Gray et al. |
| 2007/0049865 A1 | 3/2007 | Radmer et al. |
| 2007/0051784 A1 | 3/2007 | Money et al. |
| 2007/0066955 A1 | 3/2007 | Sparholt et al. |
| 2007/0066958 A1 | 3/2007 | Wright |
| 2007/0088271 A1 | 4/2007 | Richards et al. |
| 2007/0093754 A1 | 4/2007 | Mogensen |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheider et al. |
| 2007/0129691 A1 | 6/2007 | Sage, Jr. et al. |
| 2007/0173767 A1 | 7/2007 | Lynch et al. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0185441 A1 | 9/2007 | Fangrow, Jr. |
| 2007/0213673 A1 | 9/2007 | Douglas |
| 2007/0179444 A1 | 10/2007 | Causey et al. |
| 2007/0244448 A1 | 10/2007 | Lastovich et al. |
| 2007/0282269 A1* | 12/2007 | Carter ............... A61M 5/14248 604/164.01 |
| 2007/0299409 A1 | 12/2007 | Whitbourne et al. |
| 2008/0004515 A1 | 1/2008 | Jennewine |
| 2008/0058692 A1 | 3/2008 | Propp et al. |
| 2008/0119707 A1 | 5/2008 | Stafford |
| 2008/0200897 A1 | 8/2008 | Hoss et al. |
| 2008/0269687 A1 | 10/2008 | Chong et al. |
| 2008/0312601 A1 | 12/2008 | Cane' |
| 2009/0062767 A1 | 3/2009 | Van Antwerp et al. |
| 2009/0118592 A1 | 5/2009 | Klitgaard |
| 2009/0326456 A1 | 12/2009 | Cross et al. |
| 2010/0004597 A1 | 1/2010 | Gyrn et al. |
| 2010/0022956 A1 | 1/2010 | Tipsmark et al. |
| 2010/0137829 A1 | 6/2010 | Nielsen et al. |
| 2010/0228226 A1 | 9/2010 | Nielsen |
| 2010/0262078 A1 | 10/2010 | Blomquist |
| 2011/0028982 A1 | 2/2011 | Lacy |
| 2011/0054399 A1 | 3/2011 | Chong et al. |

FOREIGN PATENT DOCUMENTS

| | | |
|---|---|---|
| DE | 299 05 072 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0 272 530 A2 | 6/1988 |
| EP | 0451040 A1 | 10/1991 |

(56) References Cited

FOREIGN PATENT DOCUMENTS

| | | |
|---|---|---|
| EP | 0544837 B1 | 6/1993 |
| EP | 0615768 A2 | 9/1994 |
| EP | 0 652 027 A1 | 5/1995 |
| EP | 0651662 B1 | 5/1995 |
| EP | 0657184 A1 | 6/1995 |
| EP | 0688232 B1 | 12/1995 |
| EP | 0714631 B1 | 6/1996 |
| EP | 0744183 A2 | 11/1996 |
| EP | 0747006 A1 | 12/1996 |
| EP | 0799626 A1 | 10/1997 |
| EP | 0937475 A2 | 8/1999 |
| EP | 0956879 A1 | 11/1999 |
| EP | 2272559 A1 | 1/2001 |
| EP | 1086718 A1 | 3/2001 |
| EP | 1125593 A1 | 8/2001 |
| EP | 0775501 B1 | 6/2002 |
| EP | 1329233 B1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| FR | 2725902 A1 | 10/1994 |
| FR | 2 752 164 A1 | 2/1998 |
| GB | 906574 | 9/1962 |
| GB | 2 088 215 A | 6/1982 |
| GB | 2 230 702 A | 10/1990 |
| GB | 2 423 267 A | 8/2006 |
| GB | 2 450 872 A | 7/2007 |
| GB | 2 459 101 A | 10/2009 |
| JP | 10179734 A | 8/1991 |
| JP | 7051251 A | 11/1995 |
| JP | 8187286 A | 7/1996 |
| JP | A-03-191965 A | 7/1998 |
| JP | 2002-028246 A | 1/2002 |
| RU | 2 238 111 C2 | 12/2003 |
| SU | 933 100 | 6/1982 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/32981 A1 | 7/1996 |
| WO | WO 96/20021 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO 99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |
| WO | WO 01/68180 A1 | 9/2001 |
| WO | WO 01/72353 A2 | 10/2001 |
| WO | WO 01/076684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/040083 A2 | 5/2002 |
| WO | WO 02/053220 A2 | 7/2002 |
| WO | WO 02/081012 A2 | 10/2002 |
| WO | WO 02/081013 A2 | 10/2002 |
| WO | WO 02/083206 A2 | 10/2002 |
| WO | WO 02/083228 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 02/068014 A2 | 1/2003 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 2003/095003 A1 | 11/2003 |
| WO | WO 2004/012796 A1 | 2/2004 |
| WO | WO 2004/024219 A1 | 3/2004 |
| WO | WO 2004/026375 A1 | 4/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/112800 A2 | 12/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062680 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |

(56) References Cited

FOREIGN PATENT DOCUMENTS

| | | |
|---|---|---|
| WO | WO 2008/014791 A1 | 2/2008 |
| WO | WO 2008/014792 A1 | 2/2008 |
| WO | WO 2008/133702 A1 | 3/2008 |
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A2 | 8/2008 |
| WO | WO 2008/092959 A1 | 8/2008 |
| WO | WO 2008/135098 A1 | 11/2008 |
| WO | WO 2008/147600 A1 | 12/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/033032 A1 | 3/2009 |
| WO | WO 2009/039013 A1 | 3/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/080715 A1 | 7/2010 |
| WO | WO 2010/112521 A1 | 10/2010 |
| WO | WO 2011/012465 A1 | 2/2011 |
| WO | WO 2011/015659 A1 | 2/2011 |
| WO | WO 2011/121023 A1 | 10/2011 |
| WO | WO 2012/041784 A1 | 4/2012 |
| WO | WO 2012/041923 A2 | 4/2012 |
| WO | WO 2012/045667 A2 | 4/2012 |
| WO | WO 2012/107440 A1 | 8/2012 |
| WO | WO 2012/123274 A1 | 9/2012 |

OTHER PUBLICATIONS

"Why inset®?" inset® infusion set product overview. Printed from: http://web.archive.org/web/20040906102448/http://www.infusion-set.com/Default.asp?1D=108; 2 pages, © 2004, printed Jan. 9, 2008.

* cited by examiner

SEALING BETWEEN A CANNULA PART AND A FLUID PATH

This application claims the benefit under 35 U.S.C. § 371 of International Application No. PCT/EP2009/051634, filed Feb. 12, 2009, which claims the benefit of Danish Patent Application No. PA 2008 00202, filed Feb. 13, 2008, and U.S. Provisional Application Serial No. 61/028,259, filed Feb. 13, 2008.

THE TECHNICAL FIELD

The invention relates to an infusion part comprising a cannula part and a fluid path for providing continuous administration of a therapeutically working substance, such as insulin. The infusion part can be connected to delivery means which means provide e.g. controlled dosage of medication or nutrients.

PRIOR ART

WO 2007/071258 describes a medical device for delivering fluid comprising an injection part and a fluid delivery part where the fluid delivery part and the injection part can be separated and rejoined. The fluid delivery part comprises a reservoir, means for transport of liquid e.g. in form of a pump and a house in which the active units of the delivery part is placed. The injection part comprises: a base plate, a cannula part comprising a body with a through going opening provided with a cannula extending past the proximal side of the base plate and means for fixation of the base plate to the skin of the user e.g. in the form of a mounting pad. The cannula part is provided with one or more openings leading fluid to a hollow in the cannula part and each opening is covered with a self closing membrane. The delivery part and the injection part is assembled through a connector comprising a fluid path leading fluid from the reservoir to the through-going opening in the cannula part which fluid path comprises means for blocking access to the injection part when the connector is disconnected from the delivery part and/or the injection part. The embodiments illustrated in this document are quite complex and not easy to manufacture.

EP 652 027 discloses an infusion device to be placed on a patients skin for delivering of medication. This infusion device comprises a cannula device (10) carrying a penetrating cannula of steel. The cannula device (10) is concentric i.e. all parts of the cannula device are rotational symmetric with respect to rotation around the common axis. The cannula device (10) can slide axially and has a channel (11) with an inlet opening in the cylindrical side surface which inlet opening corresponds to an outlet opening of a channel (7) through which medication or the like is entering. Above and below the outlet of the channel (7) is placed a first and a second O-ring (8). Both O-rings (8) are placed in circular grooves in the inner surface of the surrounding the house (1). In this device the inserter and the cannula device are permanently joined together and this allows the cannula device to be at least partly inserted into a cannula opening which fits tightly around the cannula device even before insertion of the cannula device has taken place i.e. this results in that there are friction between the cannula part and the inner surface of the house during the entire insertion procedure. Also there is no teaching in this document of how to adapt the use of a soft cannula to this device.

THE INVENTION

The object of the invention is to provide an infusion part allowing the use of a soft cannula which is safe and simple to manufacture and which reduces the friction between the cannula part and the base part and therefore also the risk of incorrect positioning of the cannula part during insertion. This object is achieved by reducing the time where both the moving cannula part and the inner surface of the opening for receiving the cannula part are in contact with the gasket sealing of fluid from the surroundings. This can generally be achieved by creating a cannula part having an increasing diameter or by creating a sealing with a smaller area.

This object is achieved by an infusion part as described in claim 1 comprising a cannula part and a fluid path, where
    the cannula part comprises a body formed by a hard material which body has an inner through going opening which through going opening is in fluid contact with a cannula, the cannula has an inner opening which provides fluid contact with the patient, the body of the cannula part has an opening corresponding to the inlet or outlet opening of the fluid path resulting in fluid contact between the fluid path and the cannula part and these two corresponding openings do, when they are positioned opposite each other, allow unrestricted flow,
    the fluid path comprises at least one inlet and one outlet opening through which a fluid can enter and exit the fluid path, and
    a sealing is positioned between the cannula part and the inlet/outlet opening of the fluid path when the cannula part is in position for use in order to keep the fluid path to the cannula tight.

The sealing is surrounding the inlet/outlet opening and/or the distance $d_1$ between a centre line c of the cannula part and a point on the outer surface of the cannula part positioned at or above the upper edge of the sealing is larger than the distance $d_2$ between the centre line c of the cannula part and a point on the outer surface of the cannula part positioned at or below the lower edge of the sealing. "Upper edge of the sealing" defines the part of the sealing or gasket which has the longest distance to the patient's skin, and "lower edge of the sealing" defines the part of the sealing which has the shortest distance to the patient's skin when the infusion part according to the invention is inserted in a use position.

According to one embodiment the body of the cannula part is provided with a sealing before use or alternatively the opening of the fluid path or the surface surrounding the opening of the fluid path is provided with a sealing before use. "Provided" means that the sealing or gasket is somehow attached to the indicated surface, it might just be placed in a groove or a cavity as indicated in FIG. 9 or 10.

According to one embodiment the penetrating member is provided with attachment means assuring that the penetrating member is unreleasably attached to the base part after insertion.

According to one embodiment the body of the cannula part is provided with a sealing or gasket placed along the edge of the opening through which fluid enters or exits the cannula part.

According to one embodiment the opening of the fluid path corresponding to an opening of the cannula part is provided with a sealing placed along the edge of the opening i.e. in a short distance from the opening. "A short distance" is understood to be less than or equal to the distance equaling the diameter of the opening and if the opening is not round: less than or equal to the longest dimension of the opening.

The sealing material according to any embodiment can be hydrophobic and elastic e.g. the sealing material is made of silicone.

According to an embodiment the body of the cannula part has at least one second opening to the inner through going opening and preferably this at least one second opening to the inner through going opening is covered by a self closing membrane which membrane can be penetrated by a blunt or pointy needle and can be made of silicone.

This at least second opening can e.g. be used for insertion of the device if the cannula is a soft cannula not able to cut its way through the patients skin, then a separate insertion needle can pass through the second opening, all through the cannula and provide a cutting edge in front of the cannula. It can also be used for supplying medication or nutrients which only are given to the patient in smaller doses a few times a day.

According to an embodiment the infusion part comprises a base part which can be fastened to a patient's skin.

According to one embodiment of such an infusion part the base part is provided with an opening corresponding to the profile at the non-penetrating end of the cannula part.

The "non-penetrating end" of the cannula part is the end opposite the cannula i.e. the distal end of the penetrating member where "distal" indicates the end is turned away from the patient. In the embodiment of the cannula part shown in the FIGS. 4A, 4B and 4C the cannula part has a flat surface part on one side corresponding to a flat wall surrounding the opening of the fluid path, i.e. that the opening is "adapted" means that the surrounding walls correspond to the cannula part and assures that the cannula part ends up in a well-defined and close fitted—preferably press-fitted—position. "Press-fitted" means that it is so close fitted that it requires a force to insert the cannula part.

According to this embodiment the opening can extend below the outer surface of the base part providing walls which tightly fits around the cannula part when the cannula part is inserted into the patient and preferably the inlet or outlet opening of the fluid path opens into the wall of the opening fitting around the cannula part and when the cannula part is inserted, an inlet or outlet to the inner opening of the cannula part corresponds to the inlet/outlet opening of the fluid path.

According to one embodiment the distance $d_1$ between a centre line c of the cannula part and a point on the outer surface of the cannula part positioned at the upper edge of the sealing (18) is larger than the distance $d_2$ between the centre line c of the cannula part and a point on the outer surface of the cannula part positioned at the lower edge of the sealing. The centre line c is parallel to the direction of insertion.

According to one embodiment the angle d is the angle between the direction of insertion of the cannula part and a plane being tangent to the surface surrounding the opening opposite the sealing, and $0<d\leq90°$, normally $45\leq d\leq80°$ and most often $70\leq d\leq80°$.

When a cannula part with a decreasing cross-section is inserted into a hollow with a corresponding decreasing hollow then the cannula part can be press-fitted into the hollow. This press-fitting both assures that the two corresponding openings of respectively the fluid path and the cannula part are pressed together thereby improving the fluid tight connection between them and it can also lock the cannula part to the base part.

According to one embodiment the base part is formed at least partly of a hard material. That a material is "hard" means that it can not be penetrated by a needle, and also that it is able to maintain a shape it is given during production although it might be possible to flex the material due to the shape it is given e.g. if it is formed as a thin plate or if it is very long but it will not be possible to compress it i.e. reduce it size.

According to one embodiment the fluid path is formed as an integrated part of the base part fastened to the patient's skin. That the fluid path is formed as an integrated part means that it is an unreleasable part of the device, i.e. it is permanently attached to the device at some time during the manufacturing process of the base part and when the base part is in use it will not be possible to separate the fluid path and the rest of the base part.

According to one embodiment the hard material is a molded plastic material e.g. the plastic material is polypropylene.

According to one embodiment the base part comprises fastening means for attaching delivery means to the base part. The delivery means can comprise a connecting part provided with means corresponding to the means for fastening of delivery means and provided with a tube for transferring medication to the infusion part or the delivery means can comprise a reservoir containing medication and means for transferring medication to the infusion part. The means for transferring will normally be a pump and a programmable part possibly combined with a sensor for assuring appropriate amounts of medication to be delivered to the patient.

Embodiments of the invention will now be described with reference to the figures in which.

Figure 11A:
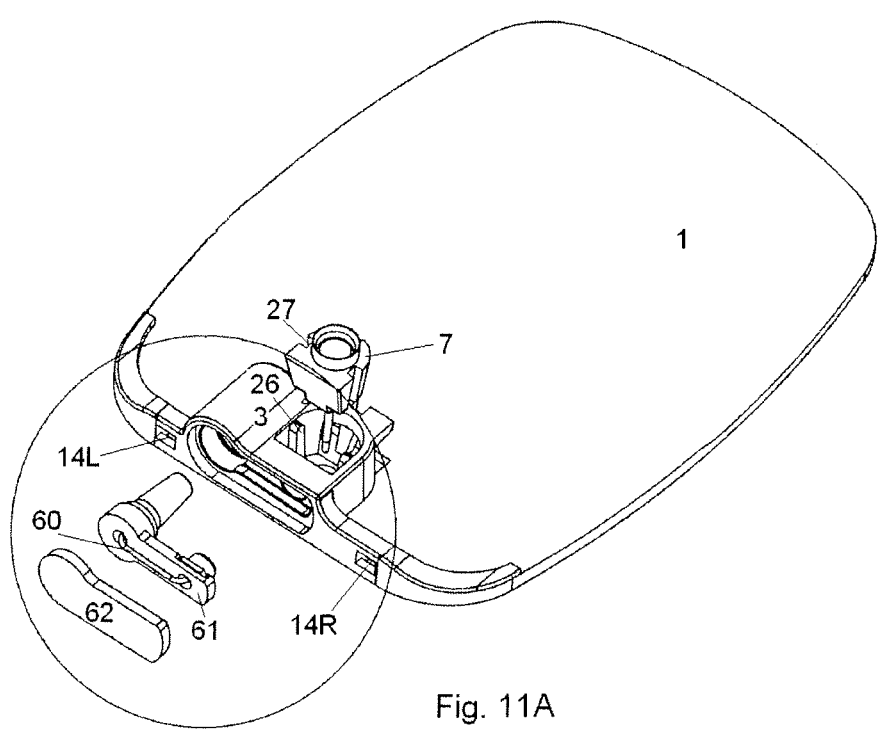

FIGS. 11A, B and C show an embodiment of a base part provided with a fluid path mainly constructed of a tube.

Figure 12:
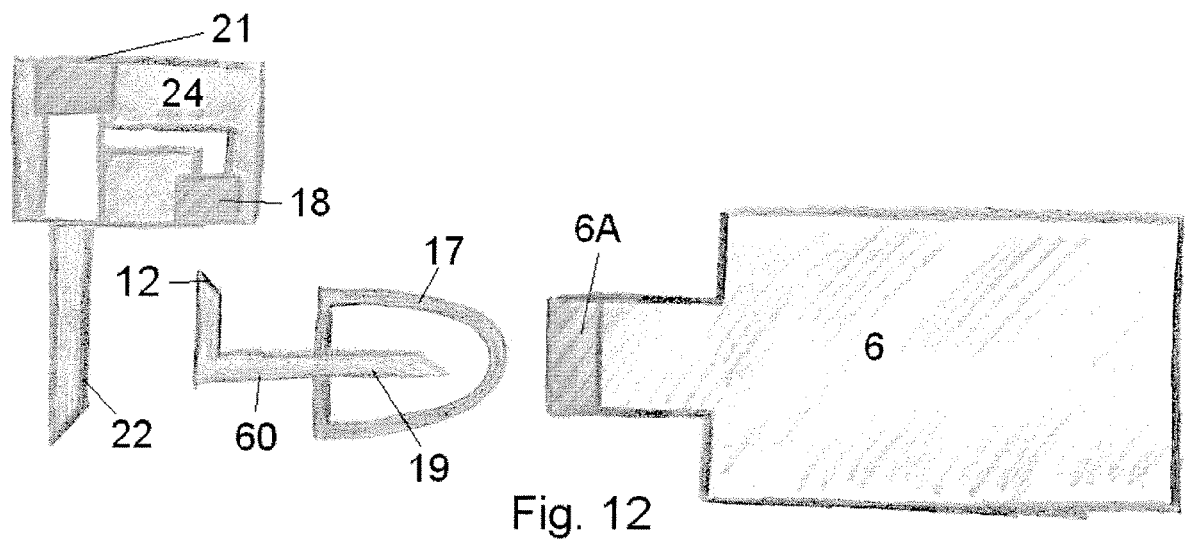

FIG. 12 shows an embodiment of an infusion part having an angle d=90° between insertion direction and tangent to contact surface.

Figure 13:
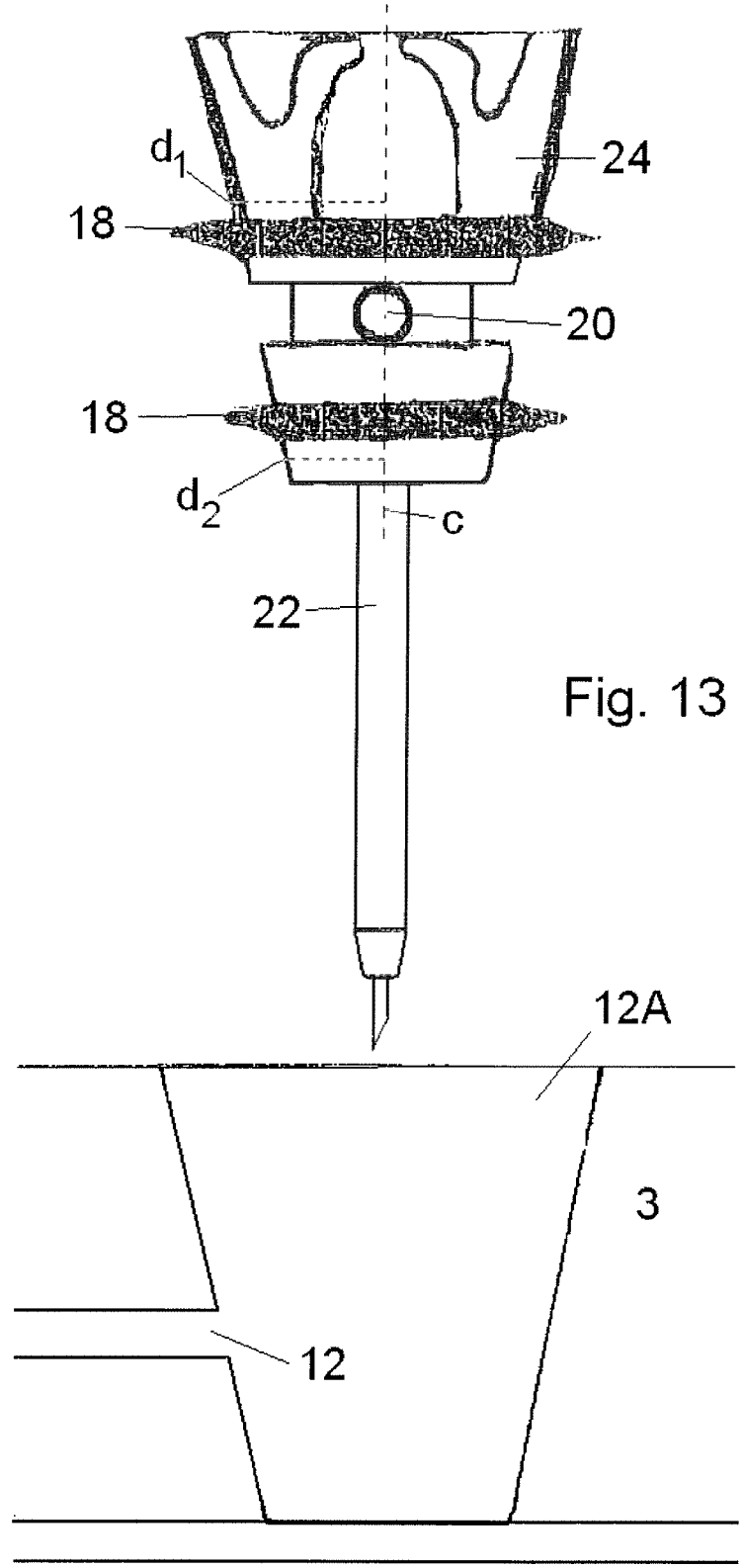

FIG. 13 shows a cannula part which can be used in connection with the invention.

Figure 1:
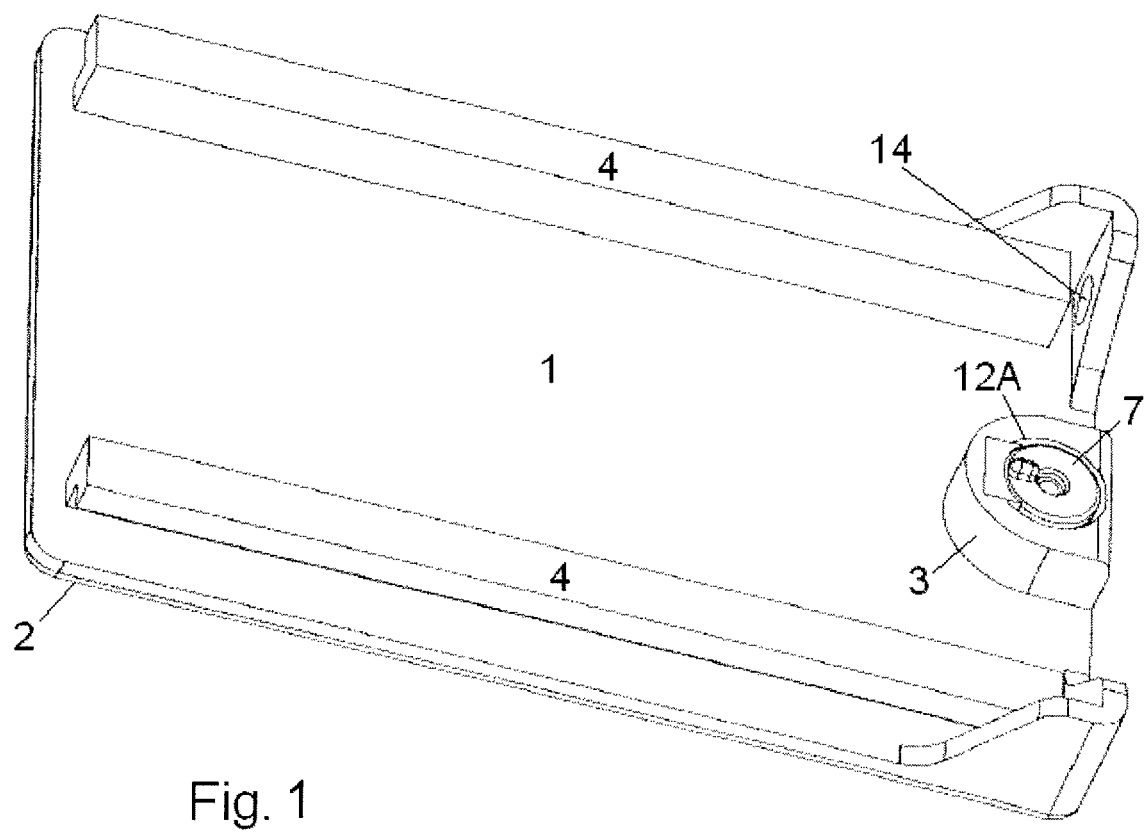
FIG. 1 shows a first embodiment of an infusion part according to the invention.

FIG. 1 shows an embodiment of an infusion part comprising a cannula part and a fluid path according to the invention. This embodiment comprises a surface plate 1 attached to a contact surface. The surface plate 1 is in this embodiment constructed of a molded plastic material and the contact surface can be the proximal side of a mounting pad 2 which mounting pad 2 is unreleasably fastened to the surface plate 1 during manufacturing of the device. The mounting pad 2 of this embodiment has the same area as the surface plate 1 but it could be of an area larger or smaller than the surface plate 1.

A connector part 3 is position on the surface plate 1. The connector part 3 provides for the contact between the base part and some kind of delivery means. According to one embodiment the surface plate 1 and at least an outer cover of the connector part 3 is simply molded in one piece during manufacturing of the device. The internal parts of the connector part 3 forms a fluid path between e.g. a reservoir of medication or a reservoir for liquid collected from the patient and a cannula part 7. Therefore the connector part 3 is provided with at least two openings, one opening at each end of the fluid path where the first opening 13 is an inlet or outlet opening receiving or delivering fluid to a not shown reservoir and the second opening is an inlet or outlet opening 12 receiving or delivering fluid to a cannula part 7. The connection part 3 might be provided with extra openings e.g. for inserting the cannula part, for injection of a second medication or nutrient or for letting the fluid in the fluid path get in contact with a sensor.

In the following the first opening 13 will be referred to as "inlet" and the second opening will be referred to as "outlet" although the direction of the flow through the fluid path is not significant for the invention.

The embodiment of FIG. 1 is provided with two guiding means 4 in the form of two right angled L-shaped profiles in the form: ] [, which profiles are protruding from the surface plate 1 of a base part having a lower or proximal side which is fastened to the skin of the patient. The guiding means 4 correspond to guiding means on a delivery part or a cover or connecting means which are to be fastened to the base part during use. Such corresponding means can e.g. be formed as one or more hooks having an L-shaped profile in the form: ⌊ and ⌋ corresponding to the profiles on the base part.

The fluid path of the connection part 3 of this embodiment is very short and the inlet 13 of the connection part 3 is placed in a centre position in relation to the guiding means 4. The top of an inserted cannula part 7 is shown inserted into the connection part 3.

The connection part 3 is further provided with a cannula cavity 12A which accurately fits around a cannula part 7 i.e. the cannula cavity 12A has the same 3-dimensional shape or profile as the cannula part 7 and is just big enough to let the cannula part 7 pass through and then fit into the opening. In FIG. 1 the cannula part 7 is shown in a position where the cannula part 7 is fully inserted. When the cannula part 7 is fully inserted, then the upper surface i.e. the distal surface of the cannula part 7 is normally at level with or at a lower level than the outer surface of the connection part 3 around the cannula cavity 12A.

When the cannula part 7 has been fully inserted into the connection part 3, an opening 20 in a side surface of a body 24 of the cannula part 7 corresponds to the opening 12 of the fluid path of the connection part 3 and fluid can flow from one part to the other. The opening 12 might in the following be referred to as an "outlet" although the direction of the flow is not significant to the invention.

Figure 2:
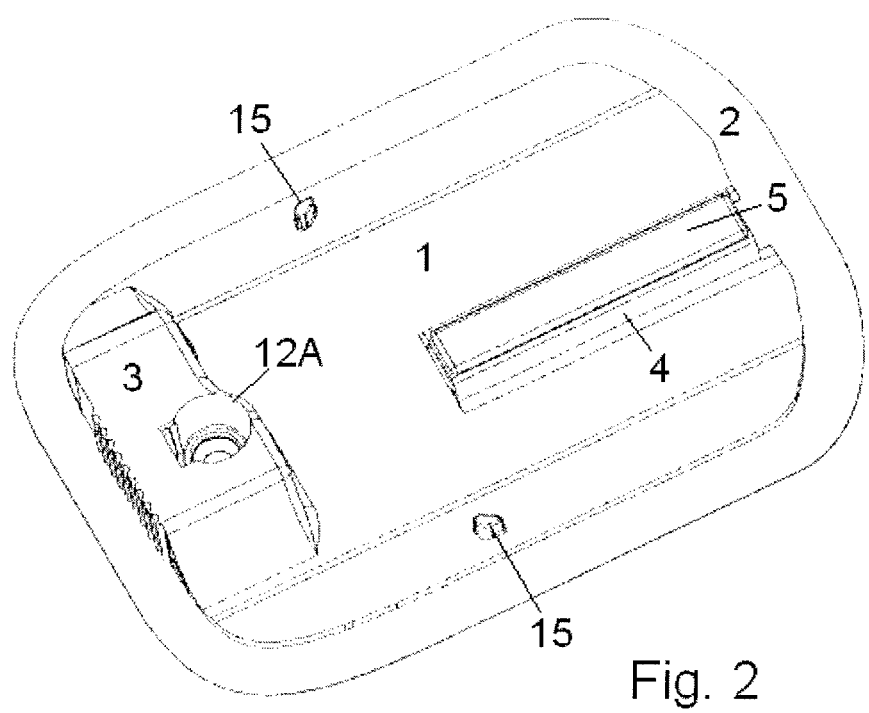
FIGS. 2 and 2A shows a second embodiment of an infusion part according to the invention.
Figure 3:
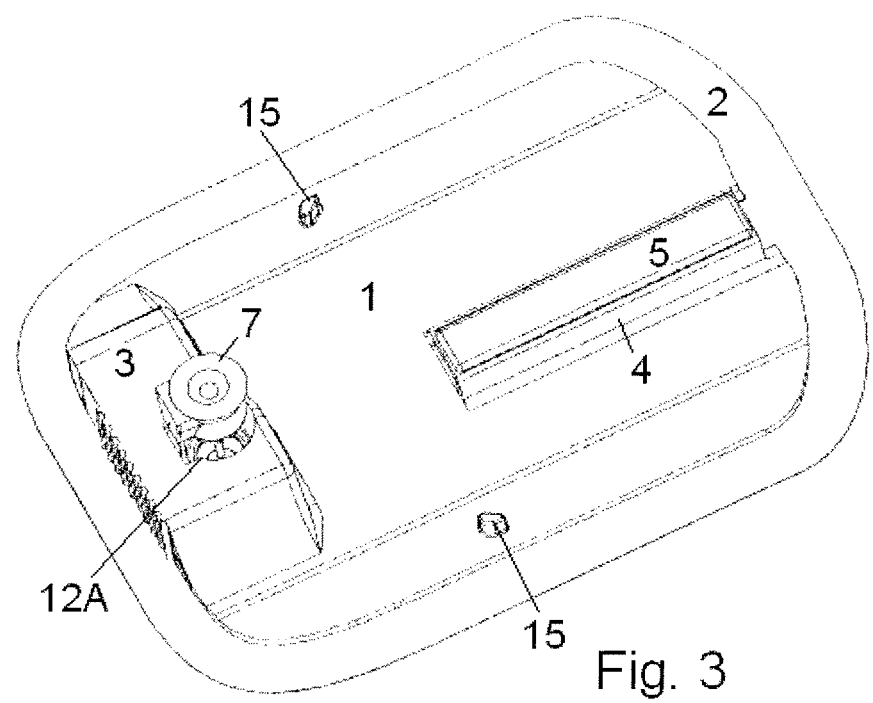
FIG. 3 shows the same embodiment of an infusion part as FIGS. 2 and 2A.

FIGS. 2 and 3 show a second embodiment of an infusion part according to the invention. A delivery part corresponding to this embodiment could be joined to the base part by pushing the delivery part down toward the guiding means 4 which in this case is a longitudinal raised platform having a magnet 5 fastened to the top surface. The delivery part would be provided with a corresponding magnet e.g. of a smaller or different size than the magnet 5 which is placed in such a way e.g. in a track corresponding to the raised platform 4, that the corresponding magnet of the delivery part can slide along the magnet 5 on the raised platform 4 of the base part in the longitudinal direction. When the delivery part arrives at its working position, two release handles can engage respectively with two protruding parts 15 protruding from the upper surface of the surface plate 1. When the delivery part is in its working position it is locked in any horizontal direction by the release handles and in the direction perpendicular to the surface plate 1 by the two corresponding magnets of respectively the delivery part and the base part. These locking mechanisms make it possible to fasten and release the delivery device from the base part as often as needed i.e. a single-use base part can be combined with a multi-use delivery part.

Figure 2A:
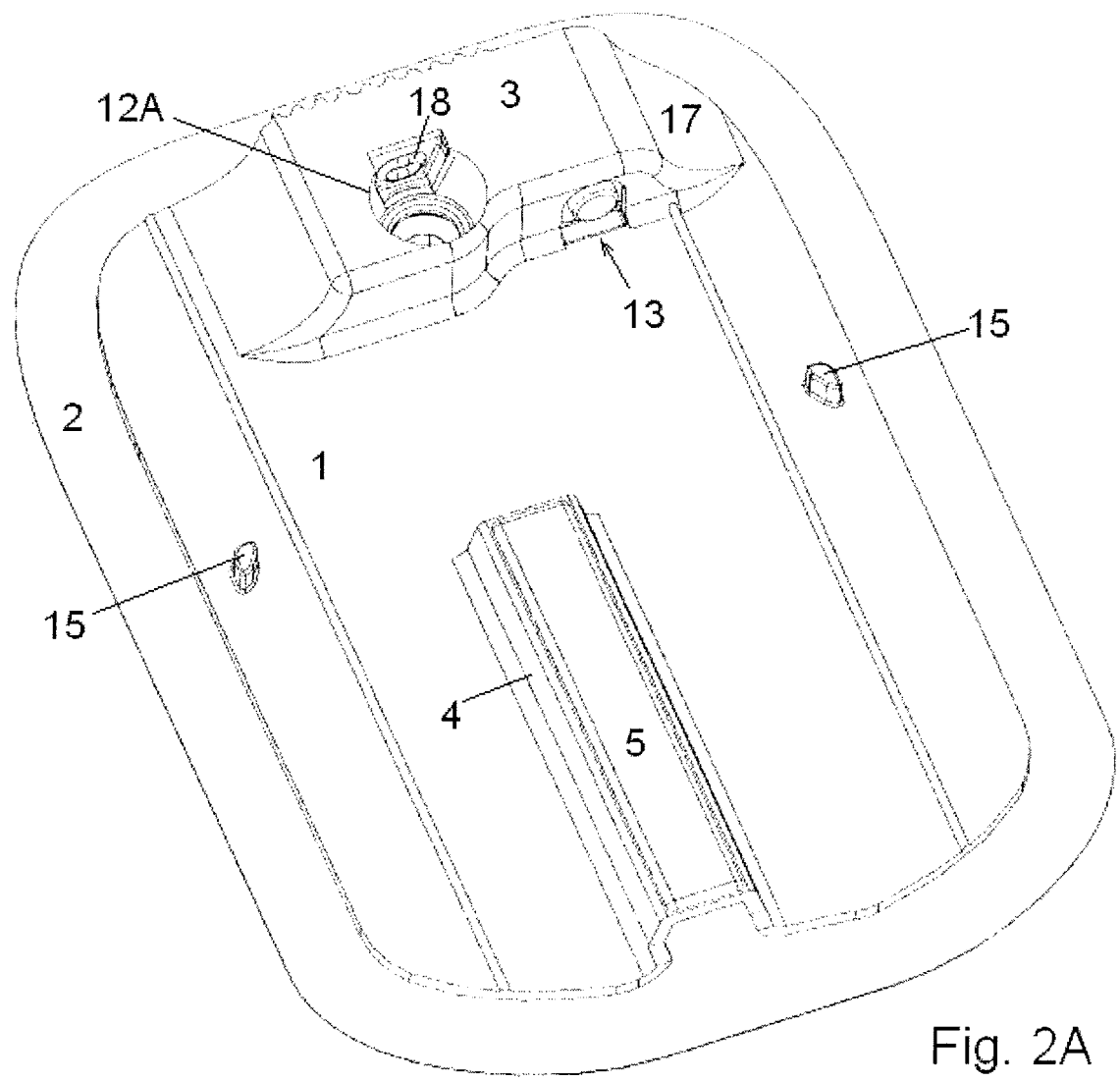

In FIGS. 2 and 2A the base part is shown without the cannula part 7 and in FIG. 3 the base part is shown having the cannula part 7 in a positioned reached just before insertion of the cannula part 7, normally the cannula part 7 would at this stage of insertion still be placed inside an inserter and it would not be visible.

Figure 5:
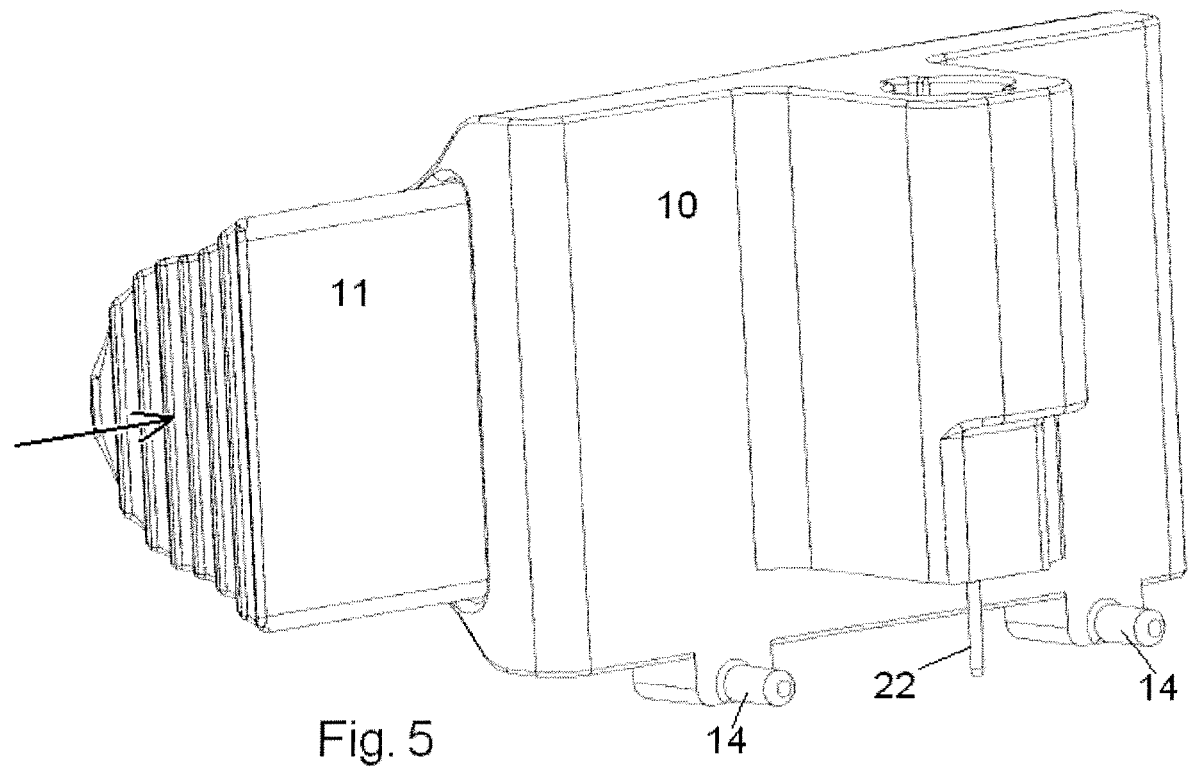
FIG. 5 shows a front view of an inserter which can be used in connection with the invention.
Figure 6:
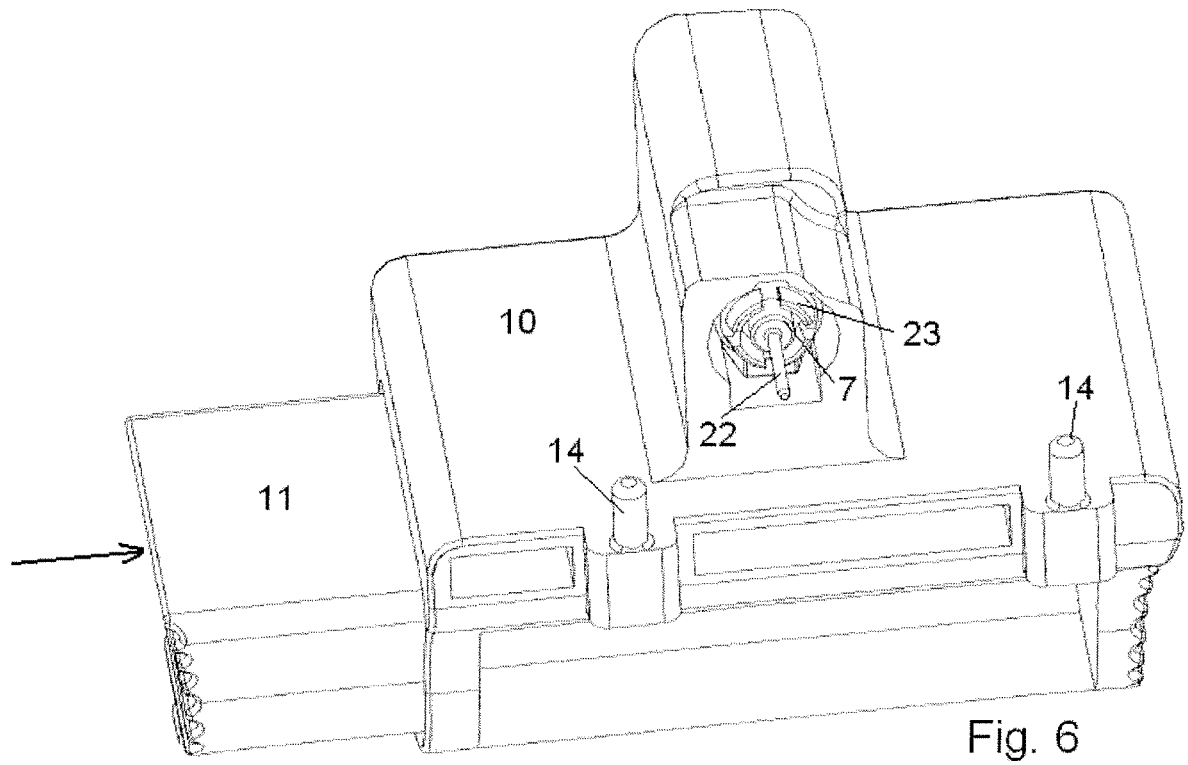
FIG. 6 shows a view from the proximal side of the inserter of FIG. 5.

Normally an inserter 10 holds the cannula part 7 before insertion and the insertion can be initiated by pushing a handle 11. FIGS. 5 and 6 shows the direction the handle 11 has to be pushed in, in order to initiate insertion of the cannula part 7. After insertion a not shown insertion needle can be retracted to the inside of the inserter 10 and the inserter 10 is removed from the base part, leaving an inserted cannula 22 fastened to the surface plate 1. If the cannula 22 of the cannula part 7 is a hard self penetrating cannula there will be no separate insertion needle and therefore no need to retract the insertion needle.

In FIGS. 2 and 2a the connection part 3 is shown with an outer cover provided by the molded surface plate 1. The outer cover shown in this embodiment is not an independent unit but is attached unreleasably to or simply made as a part of the surface plate 1 e.g. by a molding process. The outer cover is provided with a cannula cavity 12A for the cannula part 7 and an access opening 13 for e.g. a reservoir thereby allowing access to the fluid path of the connection part 3 by the reservoir and the cannula part 7. The cannula cavity 12A allows the cannula part 7 to be inserted sub- or transcutaneous into the patient within the circumference of the hard surface plate 1 and the contact surface 2 of the base part which in this embodiment is provided by a mounting pad is also provided with an opening 12B which allows for the cannula to be inserted (see FIGS. 7 and 8). This opening 12B is not necessary if the contact surface 2 is constructed of such a material and thickness that it can be penetrated by at least the cannula 22 of the cannula part 7.

Figure 7:
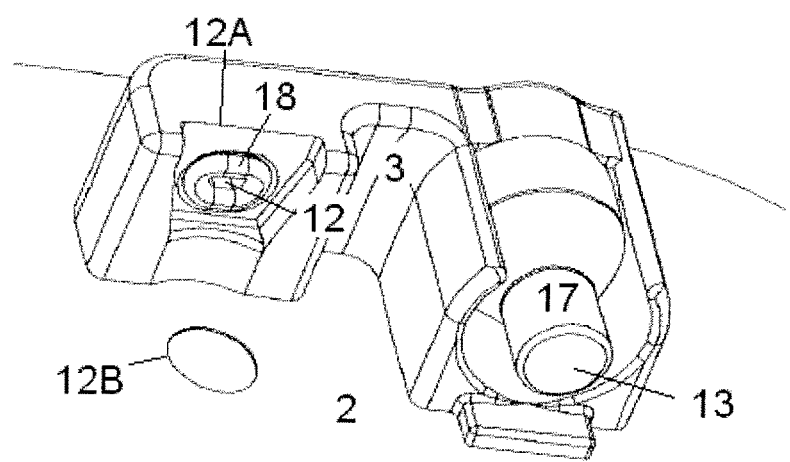
FIG. 7 shows a connector part which can be part of an infusion part according to the invention.
Figure 8:
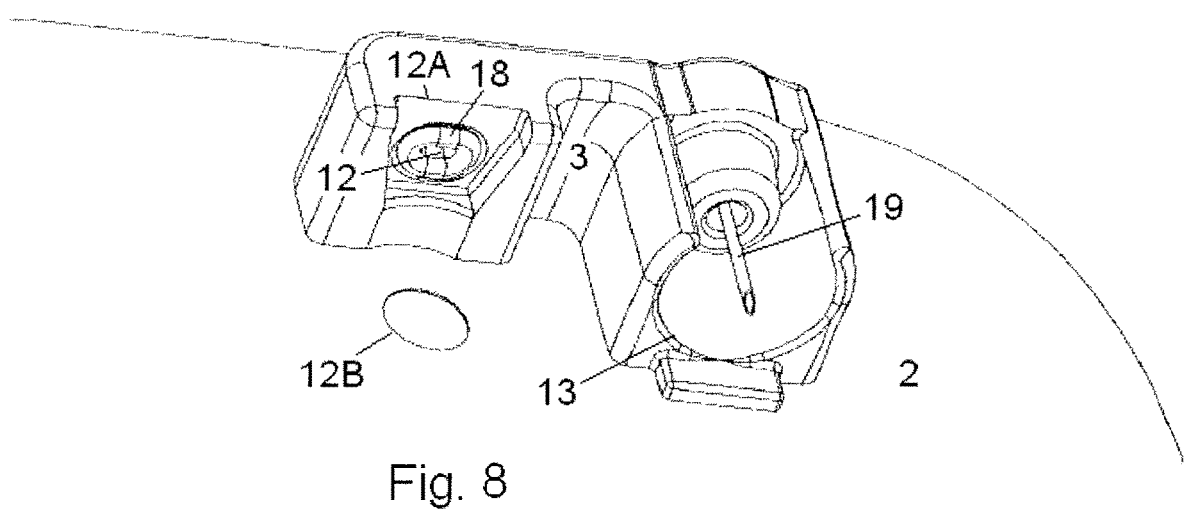
FIG. 8 shows the same connector part as FIG. 7 without the bubble membrane covering the inlet.

In FIGS. 7 and 8 the connection part 3 is shown without the outer cover provided by the molded surface plate 1. In order to secure a fluid tight connection between the outlet opening 12 in the connection part 3 and the cannula part 7 the outlet opening 12 of the connection part 3 is provided with an elastic sealing 18 around the outlet opening 12. When the cannula part 7 is inserted it will be press fitted into the cannula opening 12 and the elastic sealing 18 will provide a completely fluid tight gasket around the corresponding openings 12 and 20. In order to improved the press-fitting and thereby the fluid tight connection between the cannula part 7 and the outlet of the fluid path, the cannula cavity 12A can be provided with a decreasing cross-section in a plane parallel to the cannula 22 when inserted and perpendicular to the surface where the outlet of the fluid path is positioned. The cannula part 7 will have a corresponding decreasing cross-section.

In order to secure a fluid tight connection between the inlet opening 13 in the connection part 3 and the reservoir 6, a bubble shaped membrane 17 has been positioned around the first opening 13. The membrane 17 completely covers the inlet opening 13 and prevents contamination of the internal of the connection part 3. When a reservoir or connecting parts for a reservoir is pressed towards the connection part 3, a connector needle 19 will penetrate the membrane 17 and provide a completely fluid tight transfer of fluid between the connection part 3 and the reservoir.

That the membrane 17 is bubble shaped means that it is attached around the opening—normally around the edge of the opening—it protects and the membrane 17 protrudes from the planed formed by the edge of the opening and forms a dome in a distance from the edge which distance normally corresponds to the length of a connector needle 19.

In FIG. 8 the connector needle 19 is shown as being a part of the connection part 3 i.e. it is attached to the connection part 3 but it might just as well be a part of the reservoir.

According to one embodiment the connection part 3 is provided with both a connector needle 19 and a bubble shaped self closing membrane 17 and the reservoir is also provided with a bubble shaped self closing membrane. As both parts are provided with self closing membranes it will be possible to separate the two units from each other and rejoin them at a later time without the internal fluid path of the connection part 3 and thereby the patient being contaminated.

Figure 4A:
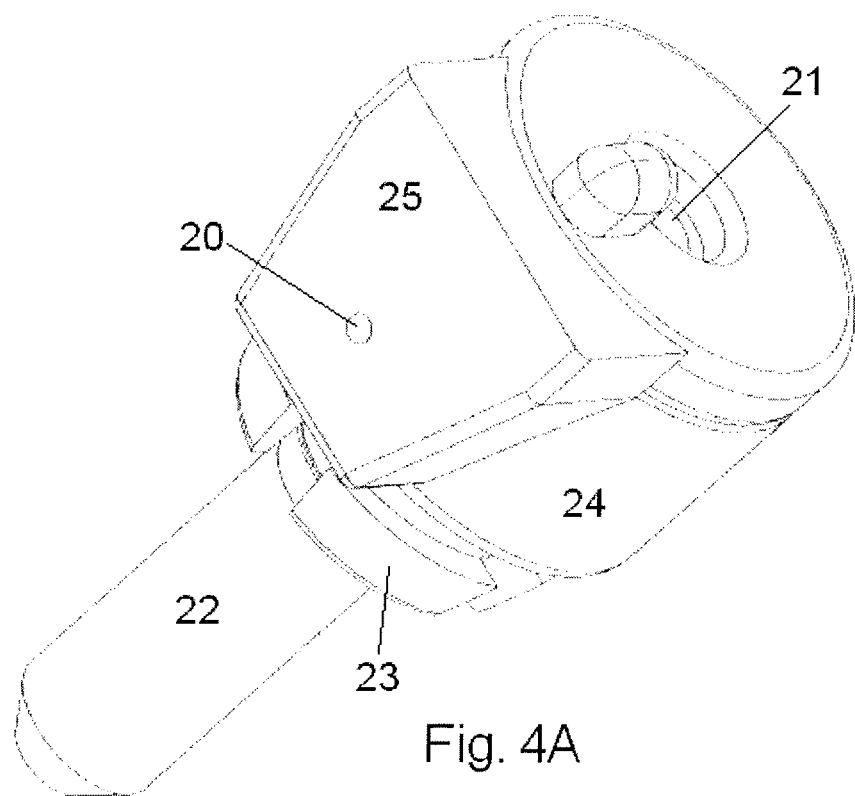
FIGS. 4A, 4B and 4C show a cannula part which can be used in connection with the invention.
Figure 4B:
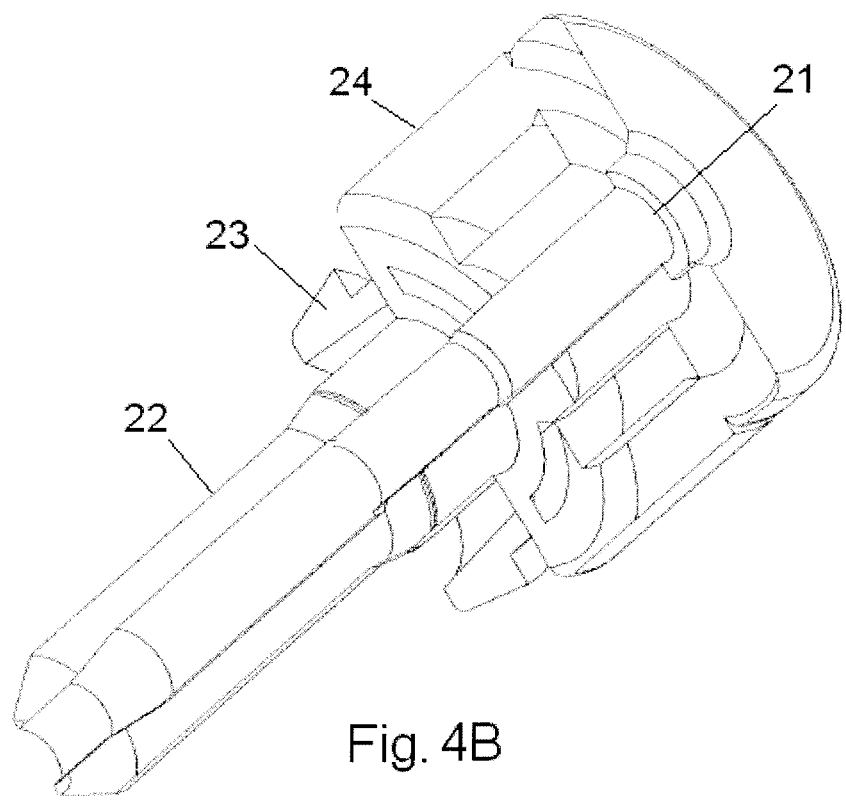
Figure 4C:
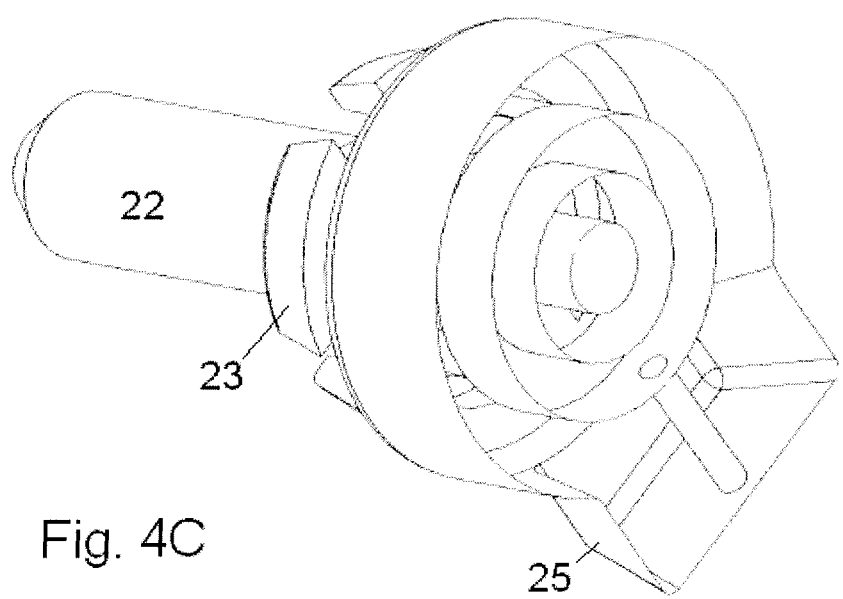

FIGS. 4A, 4B and 4C shows an enlargement of a cannula part 7 which can be used in connection with the invention. This embodiment comprises a body 24 provided with a cannula 22 and with a protruding front 25 having a flat surface. The surface of the cannula part 7 having an opening need not be flat; it can actually have any desired shape as long as it is possible to create a corresponding surface on the connection part 3 facing the cannula part 7. In one embodiment the front 25 is inclined in such a way that the cross-section at the upper i.e. distal end is larger than the cross-section at the proximal end, i.e. the enc closest to the patient after insertion, of the front in at least one dimension. The front 25 is provided with an opening 20 through which liquid can exit or enter the cannula part 7. The body 24 is further provided with a top opening 21 which opening can be covered with a self closing membrane. The opening 21 need some kind of entrance protection as it is facing an outer surface which is in contact with the surroundings. The top opening 21 is primarily used when inserting the cannula part 7 if the cannula 22 is a soft cannula. That the cannula 22 is soft means that is made of a relatively soft material which can not penetrate the patients skin, in this case it is necessary to use a pointy insertion needle of a relatively hard material when inserting the cannula and this pointy needle can be inserted through the top opening 21, pass through an inner through going opening in the body 24 of the cannula part and further pass through the full length of the cannula 22 in such a way that the pointy end of the insertion needle stick out of the open end of the hollow cannula 22. After insertion i.e. after the cannula 22 has been placed sub- or transcutaneous in the patient, then the insertion needle is retracted and the cannula 22 is left inside the patient.

The cannula part 7 is also provided with fastening means 23 which fastening means 23 lock the cannula part 7 to the base part at the time where it is fully inserted. The fastening means 23 of this embodiment comprises outward hooks that can pivot around an axe close to the body 24 of the cannula part 7 in such a way that the diameter formed by the outermost edge of the hooks can be reduced when the hooks are pressed inward i.e. towards the centre of the cannula part 7. When the pressure is removed the hooks will return to their original position due to the flexibility of the material. The hooks will be pushed inwards when they pass an opening such as e.g. the opening 12B or a corresponding opening in the surface plate having a cross-section which at least in one dimension is smaller than the outer edge of the hooks and as the hooks return to their original position after having passed through the opening, the hooks will lock the cannula part 7 in the inserted position.

FIGS. 5 and 6 show an inserter that can be used to position the cannula part 7 in the base part. The inserter comprises a housing 10 provided with an internal opening where the cannula part 7 can be moved from a retracted position to a forward position. In the retracted position the cannula 22 is not in contact with the patient and in the forward position the cannula 22 is inserted into the patient. The inserter further comprises an actuator handle 11 which is to be activated when the cannula part 7 is to be inserted and it comprises fastening means 14 which means can lock the inserter to the base part before and during insertion. Normally the inserter should be fastened to the base part under sterile conditions or the joined base part and inserter should be sterilized after fastening of the inserter in order to prevent contamination of the cannula cavity 12A, and in order to reduce the amount of material placed on the patient's skin it is desirable to be able to remove the whole of or at least part of the inserter after the cannula part 7 has been inserted.

Figure 9A:
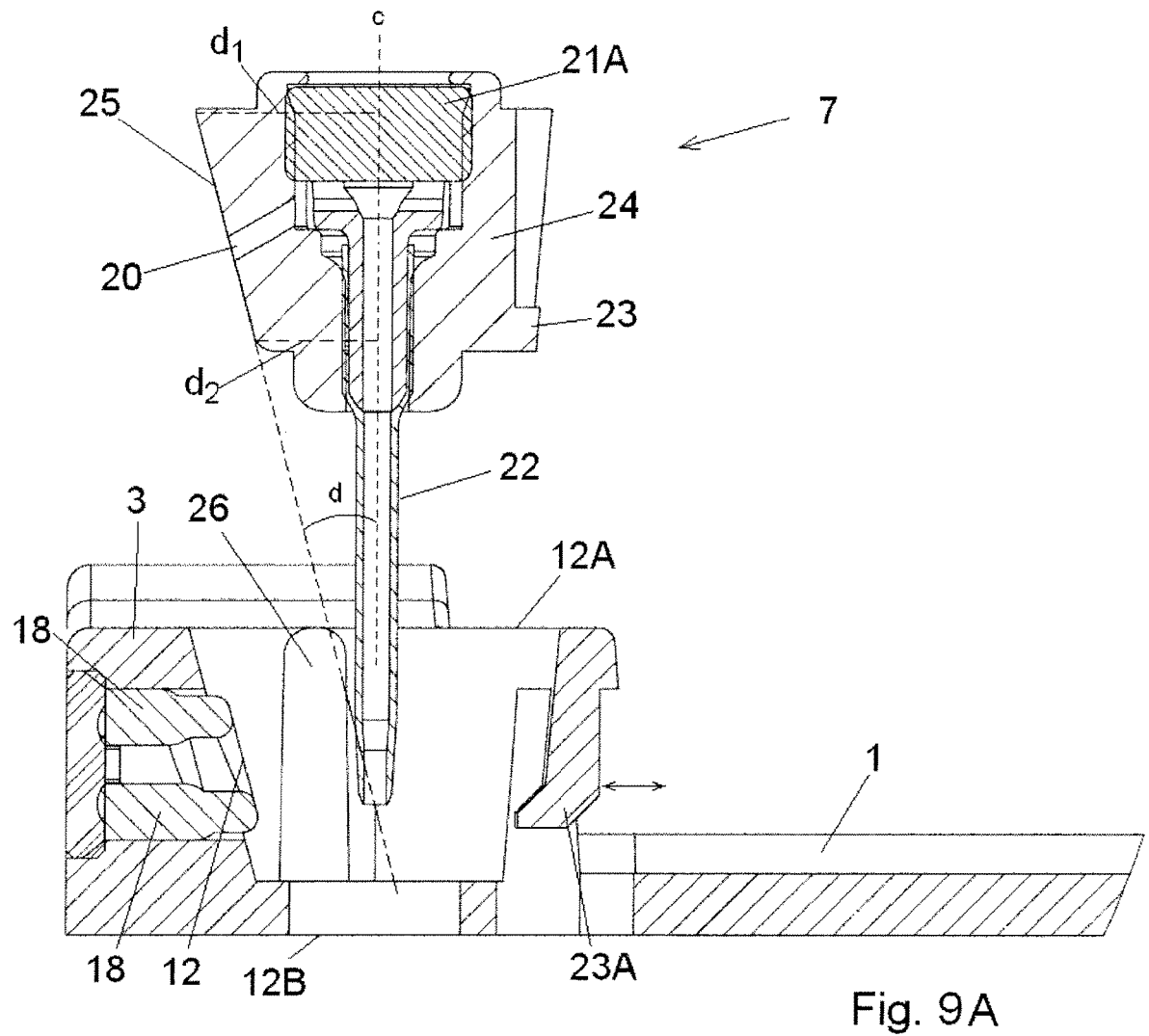
FIGS. 9A and 9B show a cannula part having an inclined contact surface.
Figure 9B:
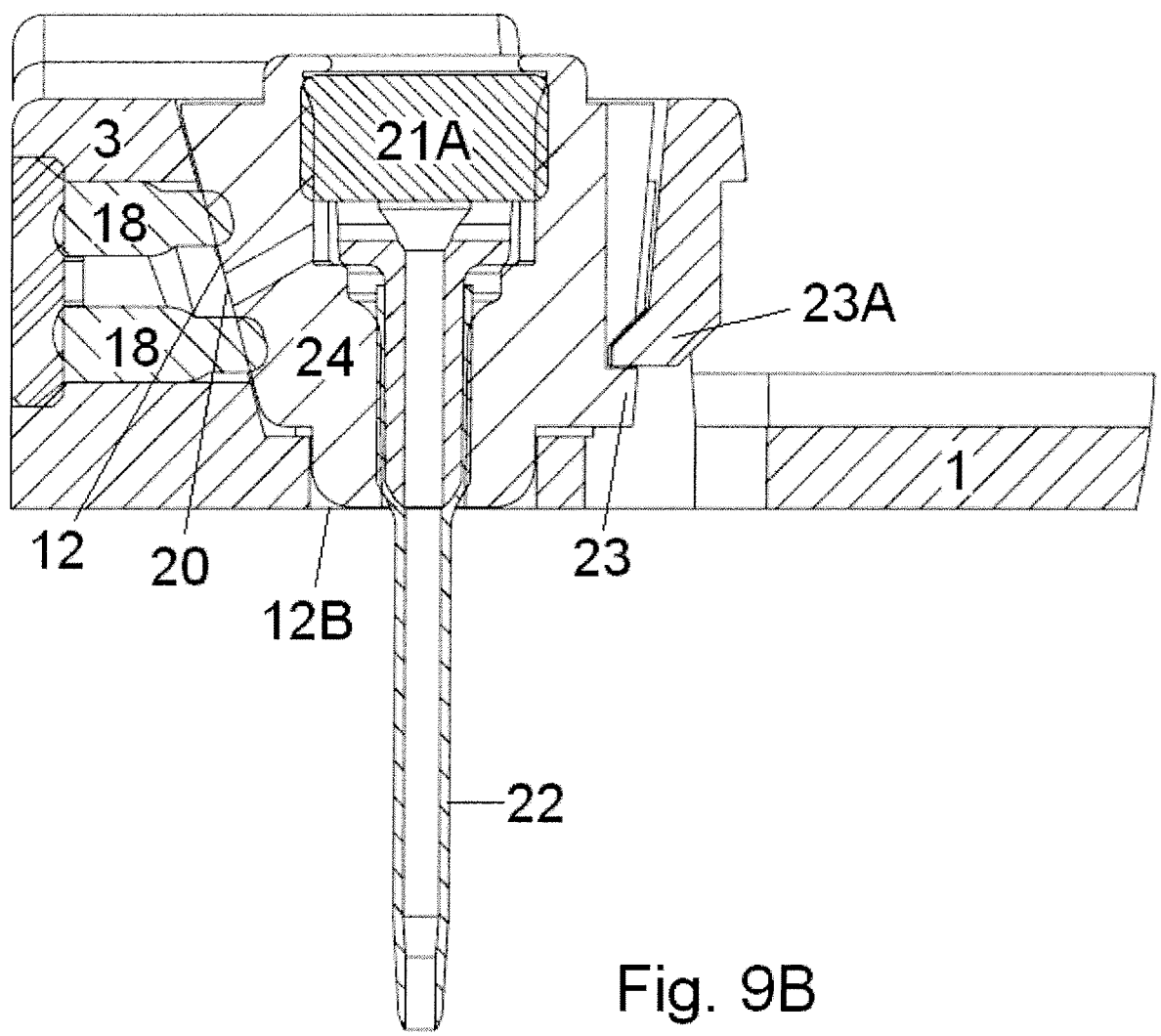

FIGS. 9A and 9B show an enlargement of a second embodiment of a cannula part 7. FIG. 9A shows the cannula part 7 in a state just before insertion and FIG. 9B shows the cannula part 7 inserted into the cavity 12A in the base part.

This embodiment also comprises a body 24 provided with a cannula 22 and with a protruding part 25 having a flat surface provided with an opening 20. According to this embodiment the protruding part 25 is inclined in such a way that the pressure between the opening 20 and the sealing 18 around the second opening 12 of the connection part 3 is increased, also the sealing 18 is subjected to less tear during insertion. The inclination of the inclined part 25 is defined by the angle d between the centre line c of the cannula 22 (the centre line c is parallel to the insertion direction) and a line parallel to the surface around the opening 20. If the surface around the opening 20 is not straight, then the line parallel to the surface would be the tangent to the surface around the opening 20. The angle d will be larger than 0° and smaller than or equal to 90°, normally $d \in ]0°, 30°]$ depending on the diameter or the protrusion of the sealing 18 or $[60°, 90°[$. The distance $d_1$ measured at the distal end of the surface of the protruding inclined part 25 where the distal end is the end of the cannula part 7 which is furthest away from the patient after insertion, between the surface of the protruding inclined part 25 and the centre c of the cannula part 7 is larger than the distance $d_2$ between the surface of the protruding part 25 at the proximal end i.e. the end closest to the patient after insertion, and the centre c of the cannula part 7. Normally the distance $d_2$ will be so small that the proximal end of the protruding inclined part 25 does not touch the sealing 18 of the connection part 3 during insertion.

In one embodiment (not shown) the angle d is close to 90° i.e. d=90°, such an embodiment would in a drawing corresponding to FIGS. 9A and 9B appear to have an upward opening 12 of the connection part 3 fitting to a downward opening 20 of the cannula part 7. This means that the force pushing the cannula part 7 toward the sealing 18 will be close to perpendicular to the contact surface of the sealing 18 and this will prevent that the sealing is distorted during insertion of the cannula part 7 by the cannula part 7 sliding along the sealing 18.

In another embodiment (shown in FIGS. 4A-C and in FIGS. 10A-B) d=0° as the protruding part 25 and the centre line c are parallel. According to this embodiment the cannula part 7 will be in sliding contact with the protruding sealing 18 which can cause the sealing to be distorted.

The protruding front 25 of the cannula part 7 need not be flat; it can actually have any desired shape e.g. partly spherical as long as it is possible to create a corresponding surface on the connection part 3 facing the cannula part 7. Also the opening 20 of the protruding front 25 can behave as an inlet or an outlet depending on the purpose of the cannula part 7. In FIGS. 9A and 9B which is a cut-through view it is shown how the top opening 21 of the body 24 is covered with a self closing membrane 21A. As according to the embodiment of FIG. 4A-C the top opening 21 is primarily used when inserting the cannula part 7 if the cannula 22 is a soft cannula but the top opening 21 can also be used to inject medication or nutrients other than the primary medication which could be e.g. insulin which the patient receive via the opening 20.

This embodiment of the cannula part 7 is also provided with fastening means 23 and in this embodiment the fastening means 23 has the form of a protruding part 23 on the cannula part 7 which corresponds to a flexible part 23A on the stationary base part. The flexible part 23A can be pushed outward as indicated with an arrow at FIG. 9A when the protruding part 23 on the cannula part 7 passes during insertion of the cannula part 7. After insertion the upward surface of the protruding part 23 of the cannula part 7 will be locked by the downward surface of the flexible part 23A of the base part and it will not be possible to detach the cannula part 7 from the base part.

The cannula part 7 of FIGS. 9A and 9B is provided with a soft cannula 22 which soft cannula 22 together with a bushing 29 provides a cannula assembly. This assembly is normally fastened inside the body 24 of the cannula part 7 by an interference fit i.e. it is only the friction between the body 24 and the cannula assembly which keeps it in the correct position. In order to prevent the cannula assembly from sliding back through the upper larger opening in the body 24 of the cannula part 7, the body 24 of the cannula part 7 can be provided with a ring shaped recess encircling the exit for the soft cannula 22. As the recess creates an open space around the soft cannula 22, the soft cannula 22 can form a small bulk i.e. a ring shaped bulk which prevents the soft cannula from sliding back.

Figure 10:
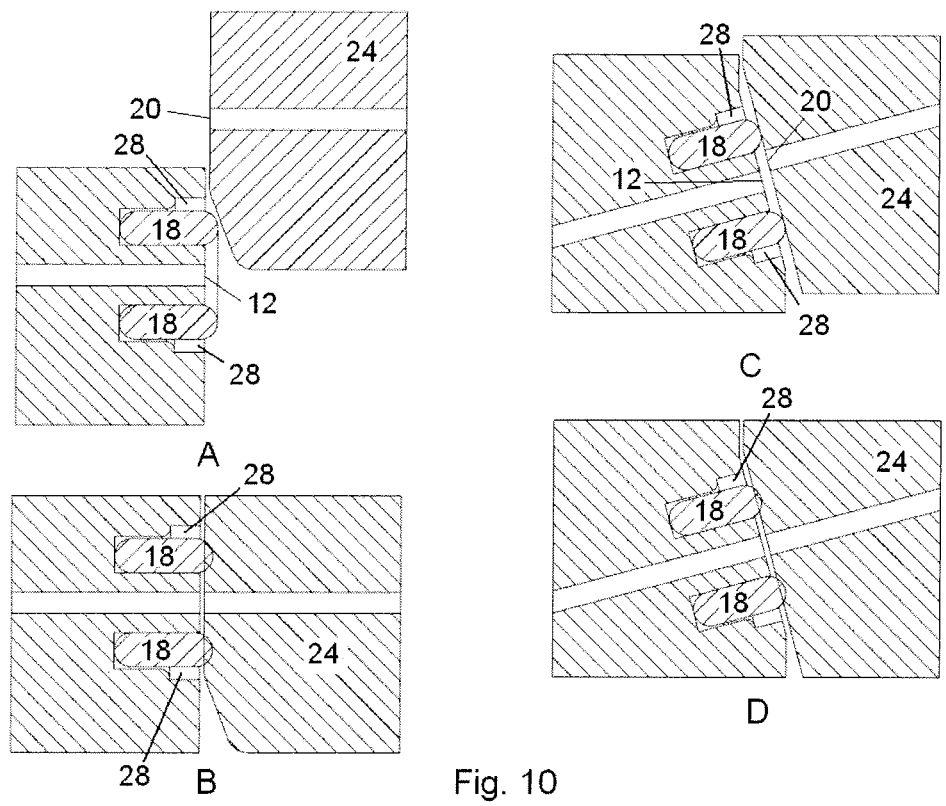
FIG. 10A-10D show an enlargement of the contact between the cannula part and the cannula opening of the connection part.

FIG. 10 illustrates how the unrestricted openings between the cannula part 7 having the body 24 and the fluid path having the inlet/outlet opening 12 slide into place. FIGS. 10A and 10B show an embodiment where d=0° and FIGS. 10C and 10D show and embodiment where d is around 15°, normally between 8-22°. According to the embodiment of FIGS. 10A and 10B the body 24 of the cannula part 7 is provided with an inclined edge in order to reduce distortion or tearing of the sealing. In both embodiments the shown sealing 18 is a circular or cylindrical silicone unit which is placed in a round track around the inlet/outlet opening 12 in the connection part 3. The wall where the sealing or gasket 18 has been placed is provided with an adjacent expansion room 28. After positioning of the cannula part 7 the sealing 18 can occupy this room. In the embodiment of FIGS. 10C and 10D is not only the sealing face angled, the whole cylindrical sealing part 18 is angled in order to allow uniform sealing deformation. The cylindrical sealing 18 does not form the walls of the inlet/outlet opening 12, the wall or surfaces of this opening is formed by the material which the connection part 3 is formed of in order to provide a pipe which cannot be deformed. In order to create the necessary pressure between the seal and the seal face i.e. the surface which the sealing 18 touches when in a sealing position, the sealing face can be provided with a small continuous protrusion protruding from the sealing face and having the same shape as the sealing which would e.g. be circular if the sealing has the cylindrical shape shown in FIG. 10A-D.

Figure 11B:
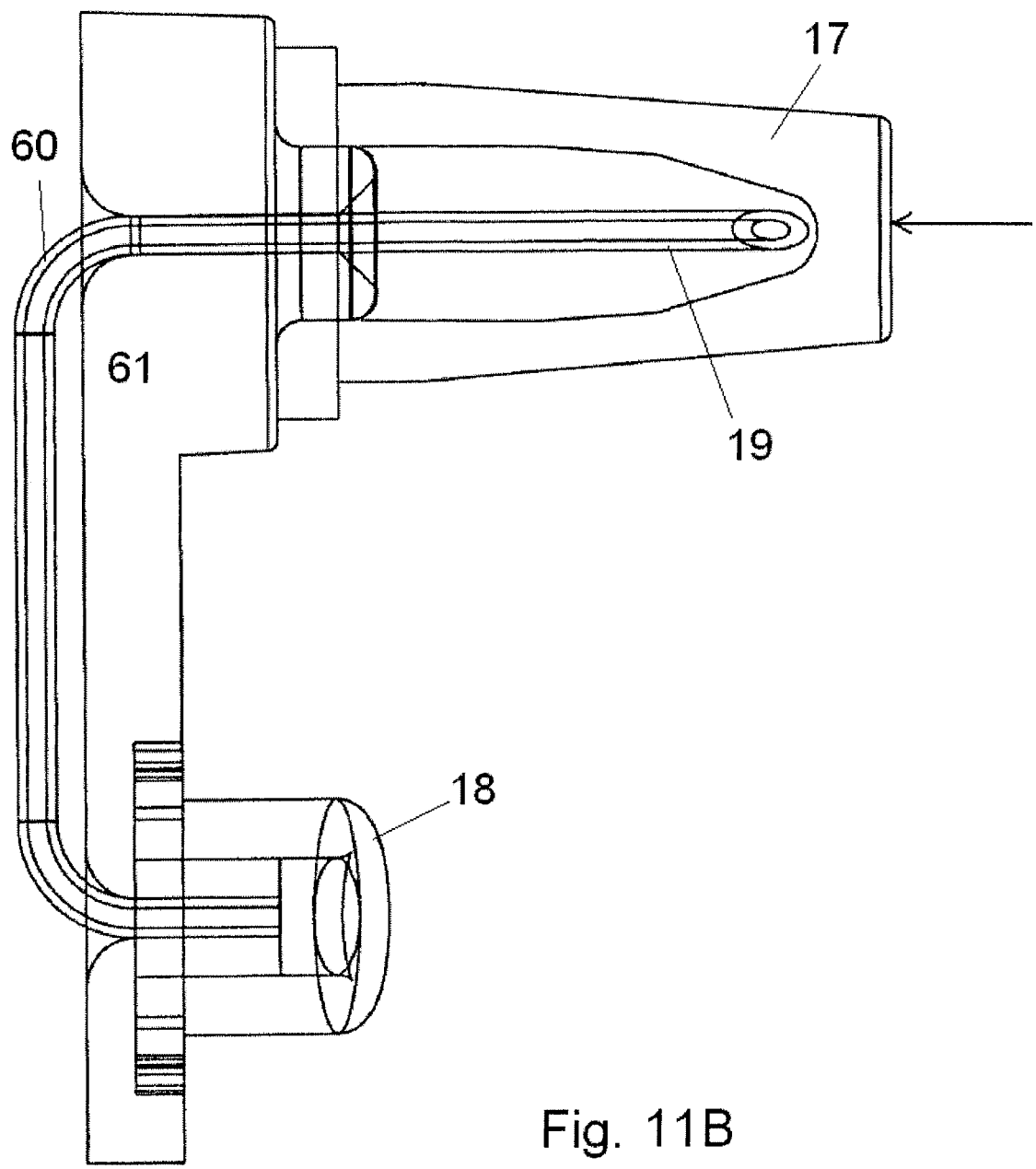
Figure 11C:
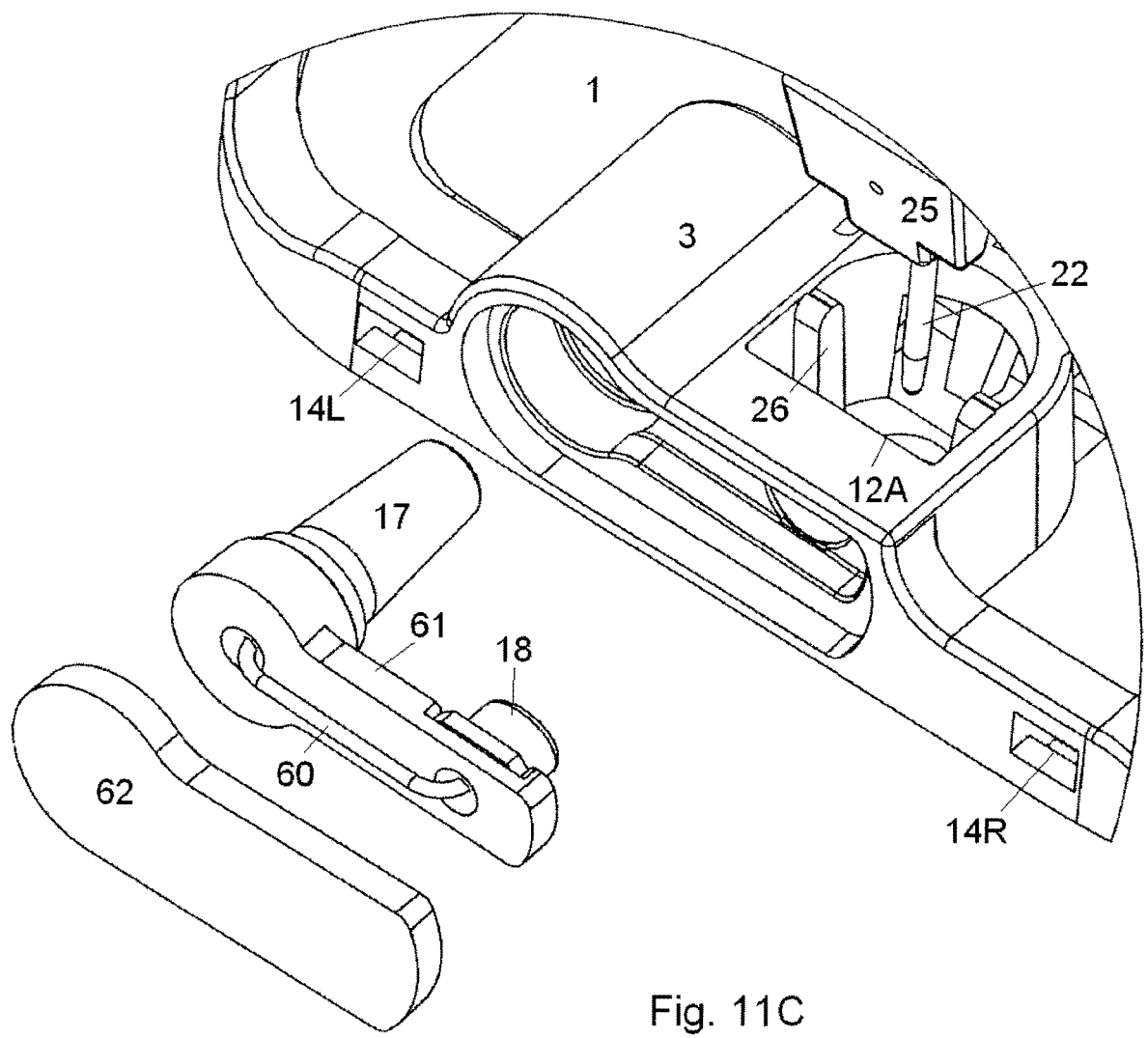

FIGS. 11A-11C show one embodiment of a connection part 3. FIG. 11A show the embodiment of the connection part 3 in an exploded view where the internal holding parts 61 for a tube 60 providing a fluid path is shown. FIG. 11B shows a cut through the internal holding part 61 according to which it is possible to the position of the tube 60. FIG. 11C shows an enlargement of the encircled part of FIG. 11A.

According to the present embodiment the connection part 3 and the surface plate 1 is molded in one piece of a plastic material, the connection part is provided with several openings, one opening is the cavity 12A which is prepared for fitting in the cannula part 7 and another opening is prepared for fitting in the internal parts of the connection part 3. The internal parts of the connection part 3 according to this embodiment comprises one tube which at two positions are bend in 90° i.e. both the inlet and the outlet end of the tube 60 points in the same direction perpendicular to the connecting part of the tube 60 where the connecting part of the tube 60 forms the fluid path between the two bending parts.

At one end the tube 60 is protected by a bubble shaped membrane 17 and at the other end the tube 60 is open and unprotected, but the open tube end is surrounded by a sealing 18 which is attached unreleasably to a holding part 61. When the internal parts have been placed in the corresponding opening in the connection part 3 a cover 62 accurately fitting in the opening is placed in level with the surface of the connection part 3 in such a way that the user experience a smooth surface which cannot be tampered with.

The embodiment of the base part shown in FIG. 11A is provided with guiding means 26 placed inside the cavity 12A of the connection part 3. The two opposing ribs 26 which constitute the guiding means correspond to closely fitting openings 27 in the cannula part 7. The guiding means 26 and the corresponding parts 27 on the cannula part can have other forms, the important feature is that they correspond to each other and make it possible for the cannula part 7 to slide into use position.

FIG. 11B shows an enlargement of the internal parts of the connection part 3. The holding parts 61 comprise a single molded part which is providing a stable embedment of the tube 60. The open end of the tube 60 opens into a space surrounded by the sealing 18. The closed end of the tube 60 is completely surrounded by a soft membrane. "Completely surrounded" means that the there is no free access to the surroundings, "soft membrane" means that the membrane can be penetrated by a needle, especially the connector needle 19 which is provided by the end of the tube 60 and which is embedded inside the soft membrane. The end of the tube 60 which constitutes the connector needle 19 is in this embodiment not actually in touch with the surrounding membrane 17. The connector needle 19 is surrounded by air, and the internal space surrounding the connector needle 19 has a cylindrical or conical shape i.e. a circular cross-section. The walls of the membrane 17 will deform by bending inwards or outwards when the length of the membrane is reduced as a result of the applied pressure.

FIG. 11C shows an enlargement of the enclosed field marked in FIG. 11A.

FIG. 12 shows an embodiment of an infusion part where the angle d=90°. The inlet/outlet opening 12 is constructed as a pointy end of a tube 60 which provide for the fluid path or connection between the reservoir 6 and the cannula part 7. A membrane e.g. self closing protects the entrance to the reservoir 6 which means that micro organisms cannot access the reservoir 6 when the reservoir is removed from the connection part 3.

FIG. 13 shows yet an embodiment of a cannula part 7 which can be used with an infusion part according to claim 1. The body 24 of the cannula part 7 has the shape or profile of a truncated cone i.e. in each horizontal (according to FIG. 13) cross-section of the body it is round having varying diameters. The body 24 is provided with two permanently attached circular sealings or gaskets 18. Between these two gaskets 18 is the opening 20 positioned which opening 20 allows for fluid to enter the inner through going opening of the cannula part 7. The cannula part 7 is to be placed in a below illustrated connection part 3 provided with a corresponding cavity 12A also having the shape of a truncated cone. The cavity 12A has an inlet/outlet opening 12 for fluid flowing to or from the cannula 22.

The invention claimed is:

1. An infusion part comprising:
   a base part attached to a patient's skin during use, the base part comprising a connector part, the connector part comprising a fluid path, the fluid path comprising two fluid path openings, wherein each fluid path opening of the two fluid path openings is an inlet opening or an outlet opening;
   a cannula part, comprising a body and a cannula, the body comprised of a hard material contacting at least a part of the cannula, the cannula attached to the body, and having an inner through going opening in fluid contact with the cannula, the cannula comprising a center line, wherein the center line is straight and perpendicular to a surface of the base part configured to be aligned with the patient's skin before insertion into the patient, and the cannula has an inner opening providing fluid contact with the patient, the body of the cannula part comprising a protruding front part comprising a flat surface, wherein the protruding front part of the cannula part comprises an opening defined through the flat surface and corresponding to one of the two fluid path openings of the connector part, wherein fluid flow through the cannula part to the patient is allowed when the opening of the protruding front part of the cannula part is positioned opposite of the one of the two fluid path openings of the connector part, and wherein the protruding front part comprising the flat surface has an inclination defined by an angle d between the center line of the cannula and the flat surface of the protruding front part, wherein the angle d is such that $0° < d < 90°$; and
   a sealing part positioned between the cannula part and the one of the two fluid path openings when the cannula part is in position for use, wherein the sealing part is provided on the connector part around the one of the two fluid path openings when the cannula part is in position for use, wherein a material of the sealing part is elastic;
   wherein, the base part further comprises a cavity corresponding to the cannula part, and the cavity comprises walls that are adapted to press-fit the cannula part when the cannula part is being inserted into the patient, and wherein the cannula is capable of being inserted into the patient along a direction of insertion.

2. The infusion part according to claim 1, wherein the connector part is provided with the sealing part before use, and wherein the sealing part is provided in a round track surrounding the one of the two fluid path openings.

3. The infusion part according to claim 1, wherein the material of the sealing part is hydrophobic and elastic.

4. The infusion part according to claim 1, wherein the material of the sealing part comprises silicone.

5. The infusion part according to claim 1, wherein the body of the cannula part has at least a second opening to the inner through going opening.

6. The infusion part according to claim 5, wherein the second opening to the inner through going opening is covered by a self closing membrane, and wherein the membrane is penetrable by a blunt or pointed needle.

7. The infusion part according claim 1, wherein the cavity extends below an outer surface of the base part providing the walls that tightly fit around the cannula part when the cannula part is inserted into the patient.

8. The infusion part according to claim 7, wherein the one of the two fluid path openings opens into the walls of the cavity fitting around the cannula part and when the cannula part is inserted, the opening of the protruding front part corresponds to the one of the two fluid path openings.

9. The infusion part according to claim 1, wherein the base part comprises a hard material.

10. The infusion part according to claim 9, wherein the hard material is a molded plastic material.

11. The infusion part according to claim 1, wherein the two fluid path openings are formed as an integrated part of the base part.

12. The infusion part according to claim 1, wherein the cannula part is provided separate from and connectable to the base part to allow fluid flow.

13. The infusion part according to claim 12, wherein the cannula part is connectable to the base part with an inserter.

14. The infusion part according to claim 1, further wherein, the fluid path is defined through a tube that is selectively coupled to the connector part.

15. An infusion assembly, comprising:
   a plate configured to be positioned adjacent to a patient's skin;
   a connector part coupled to, or formed from, the plate, the connector part having a fluid path defined from a cannula cavity to an access opening;
   a cannula part configured to be selectively received at least partially within the cannula cavity, the cannula part comprising:
      a body;
      a cannula coupled to the body along a center line and configured to extend past the plate to contact the patient when the cannula part is positioned at least partially within the cannula cavity; and
      a body opening defined through the body and angularly offset relative to the center line by an angle larger than 0 degrees and smaller than 90 degrees, the body opening providing a fluid path through the body to the cannula;
   a first fluid path opening at the cannula cavity positioned to be at least partially aligned with the body opening when the cannula part is positioned within the cannula cavity; and
   a sealing positioned to fluidly seal the body opening with the first fluid path opening when the cannula part is positioned within the cannula cavity.

16. The infusion assembly of claim 15, further wherein the body has a protruding front having a flat surface that is alignable with the first fluid path opening.

17. The infusion assembly of claim 16, further wherein the body opening is defined through the flat surface.

18. The infusion assembly of claim 17, further wherein the flat surface is inclined relative to the center line.

19. The infusion assembly of claim 15, further wherein the access opening comprises a connector needle substantially surrounded by a self closing membrane, wherein when the cannula part is positioned at least partially within the cannula cavity the cannula is fluidly coupled to the connector needle.

\* \* \* \* \*